(12) United States Patent
Miller et al.

(10) Patent No.: US 7,914,796 B2
(45) Date of Patent: Mar. 29, 2011

(54) ENGINEERED CLEAVAGE HALF-DOMAINS

(75) Inventors: Jeffrey C. Miller, San Leandro, CA (US); Michael C. Holmes, Oakland, CA (US); Gregory J. Cost, Berkeley, CA (US)

(73) Assignee: Sangamo Biosciences, Inc., Richmond, CA (US)

(*) Notice: Subject to any disclaimer, the term of this patent is extended or adjusted under 35 U.S.C. 154(b) by 183 days.

(21) Appl. No.: 12/217,185

(22) Filed: Jul. 2, 2008

(65) Prior Publication Data

US 2009/0311787 A1    Dec. 17, 2009

Related U.S. Application Data

(63) Continuation of application No. 11/805,850, filed on May 23, 2007, now abandoned.

(60) Provisional application No. 60/808,486, filed on May 25, 2006.

(51) Int. Cl.
| | |
|---|---|
| *A61K 39/00* | (2006.01) |
| *C07K 1/00* | (2006.01) |
| *C07H 21/02* | (2006.01) |
| *C12N 15/63* | (2006.01) |
| *C12N 15/87* | (2006.01) |

(52) U.S. Cl. .................. 424/192.1; 530/350; 536/23.1; 435/455; 435/463

(58) Field of Classification Search ............... 424/192.1; 530/350; 536/23.1; 435/455, 463
See application file for complete search history.

(56) References Cited

U.S. PATENT DOCUMENTS

| | | | |
|---|---|---|---|
| 4,186,183 A | 1/1980 | Steck et al. |
| 4,217,344 A | 8/1980 | Vanlerberghe et al. |
| 4,235,871 A | 11/1980 | Papahadjopoulos et al. |
| 4,261,975 A | 4/1981 | Fullerton et al. |
| 4,485,054 A | 11/1984 | Mezei et al. |
| 4,501,728 A | 2/1985 | Geho et al. |
| 4,774,085 A | 9/1988 | Fidler |
| 4,837,028 A | 6/1989 | Allen |
| 4,897,355 A | 1/1990 | Eppstein et al. |
| 4,946,787 A | 8/1990 | Eppstein et al. |
| 5,049,386 A | 9/1991 | Eppstein et al. |
| 5,173,414 A | 12/1992 | Lebkowski et al. |
| 5,176,996 A | 1/1993 | Hogan et al. |
| 5,422,251 A | 6/1995 | Fresco |
| 5,585,245 A | 12/1996 | Johnsson et al. |
| 5,789,538 A | 8/1998 | Rebar et al. |
| 5,925,523 A | 7/1999 | Dove et al. |
| 5,928,638 A | 7/1999 | Uchida et al. |
| 6,007,988 A | 12/1999 | Choo et al. |
| 6,013,453 A | 1/2000 | Choo et al. |
| 6,140,081 A | 10/2000 | Barbas |
| 6,200,759 B1 | 3/2001 | Dove et al. |
| 6,453,242 B1 | 9/2002 | Eisenberg et al. |
| 6,503,717 B2 | 1/2003 | Case et al. |
| 6,534,261 B1 | 3/2003 | Cox et al. |
| 6,599,692 B1 | 7/2003 | Case et al. |
| 6,607,882 B1 | 8/2003 | Cox, III et al. |
| 6,689,558 B2 | 2/2004 | Case |
| 6,824,978 B1 | 11/2004 | Cox, III et al. |
| 6,933,113 B2 | 8/2005 | Case et al. |
| 6,979,539 B2 | 12/2005 | Cox, III et al. |
| 7,013,219 B2 | 3/2006 | Case et al. |
| 7,163,824 B2 | 1/2007 | Cox, III et al. |
| 2003/0232410 A1 | 12/2003 | Liljedahl et al. |
| 2005/0014791 A1 | 1/2005 | Tsantrizos et al. |
| 2005/0026157 A1 | 2/2005 | Baltimore |
| 2005/0064474 A1 | 3/2005 | Urnov et al. |
| 2005/0208489 A1 | 9/2005 | Carroll |
| 2006/0063231 A1 | 3/2006 | Li et al. |
| 2006/0188987 A1 | 8/2006 | Guschan et al. |

FOREIGN PATENT DOCUMENTS

| | | |
|---|---|---|
| WO | WO 91/16024 A1 | 10/1991 |
| WO | WO 91/17424 A1 | 11/1991 |
| WO | WO 93/24641 A2 | 2/1993 |
| WO | WO 95/19431 A1 | 7/1995 |
| WO | WO 96/06166 A1 | 2/1996 |
| WO | WO 98/44350 A1 | 10/1998 |
| WO | WO 98/53057 A1 | 11/1998 |
| WO | WO 98/53058 A1 | 11/1998 |
| WO | WO 98/53059 A1 | 11/1998 |
| WO | WO 98/53060 A1 | 11/1998 |
| WO | WO 98/54311 A1 | 12/1998 |
| WO | WO 00/27878 A1 | 5/2000 |
| WO | WO 01/60970 A2 | 8/2001 |
| WO | WO 01/88197 A2 | 11/2001 |
| WO | WO 02/16536 A1 | 2/2002 |
| WO | WO 02/099084 A2 | 12/2002 |
| WO | WO 03/016496 A2 | 2/2003 |
| WO | WO 2005/084190 A2 | 9/2005 |
| WO | WO 2007/014275 A2 | 1/2007 |

OTHER PUBLICATIONS

Verma et al., 1997, Nature, vol. 389, pp. 239-242.*
Eck et al., 1996, Goodman & Gilman's The Pharmacological Basis of Therapeutics, McGraw-Hill, New York, p. 77-101.*
Kodama et al., 2006, Current Medicinal Chemistry, vol. 13, p. 2155-2161.*
Nishikawa et al., 2001, Human Gene Therapy, vol. 12, p. 861-870.*
Skolnick et al., 2000, Trends in Biotech, vol. 18, p. 34-39.*
Smallwood et al., 2002 Virology, vol. 304, p. 135-145.*
Chattopadhyay et al., 2004, Virus Research, vol. 99, p. 139-145.*
Ahmad, et al., "Antibody-Mediated Specific Binding and Cytotoxicity of Liposome-Entrapped Doxorubicin to Lung Cancer Cells In Vitro," *Cancer Res* 52(17):4817-4820 (1992).
Alvarez, et al. "A Phase I Study of Recombinant Adenovirus Vector-Mediated Intraperitoneal Delivery of Herpes Simplex Virus Thymidine Kinase (HSV-TK) Gene and Intravenous Ganciclovir for Previously Treated Ovarian and Extraovarian Cancer Patients," *Hum. Gene Ther.* 8(5):597-613 (1997).

(Continued)

*Primary Examiner* — Shin-Lin Chen
(74) *Attorney, Agent, or Firm* — Dahna S. Pasternak; Robins & Pasternak LLP

(57) ABSTRACT

Disclosed herein are engineered cleavage half-domains; fusion polypeptides comprising these engineered cleavage half-domains; polynucleotides encoding the engineered cleavage half-domains and fusion proteins; and cells comprising these polynucleotides and/or fusion proteins. Also described are methods of using these polypeptides and polynucleotides, for example for targeted cleavage of a genomic sequence.

19 Claims, 6 Drawing Sheets

OTHER PUBLICATIONS

Anderson, et al., "Phosphorylation and Rapid Relocalization of 53BP1 to Nuclear Foci Upon DNA Damage," *Mol Cell Biol* 21:1719-1729 (2001).

Anderson, "Human Gene Therapy," *Science* 256(5058):808-813 (1992).

Atwell, et al., "Stable Heterodimers From Remodeling the Domain Interface of a Homodimer Using a Phage Display Library," *J Mol Biol* 270:26-35 (1997).

Behr, et al., "Gene Transfer With Synthetic Cationic Amphiphiles: Prospects for Gene Therapy," *Bioconjug. Chem.* 5(5):382-389 (1994).

Bitinate, et al., "FokI Dimerization Is Required for DNA Cleavage," *PNAS USA* 95:10570-10575 (1998).

Blaese, et al., "Vectors in Cancer Therapy: How Will They Deliver?" *Cancer Gene Therapy* 2:291-297 (1995).

Blaese, et al., "T Lymphocyte-Directed Gene Therapy for ADA-SCID: Initial Trial Results After 4 Years," *Science* 270(5235):475-480 (1995).

Bolon, et al., "Specificity Versus Stability in Computational Protein Design," *PNAS USA* 102:12724-12729 (2005).

Buchscacchher, et al., "Human Immunodeficiency Virus Vectors for Inducible Expression of Foreign Genes," *J Virol* 66(5):2731-2739 (1992).

Crystal, "Transfer of Genes to Humans: Early Lessons and Obstacles to Success," *Science* 270(5235):404-410 (1995).

Dillon, "Regulating Gene Expression in Gene Therapy," *TIBTECH* 11(5):167-175 (1993).

Dranoff, et al., "A Phase I Study of Vaccination With Autologous, Irradiated Melanoma Cells Engineered to Secrete Human Granulocyte-Macrophage Colony Stimulating Factor," *Hum Gene Ther.* 8(1):111-112 (1997).

Dull, et al., "A Third-Generation Lentivirus Vector With a Conditional Packaging System," *J. Virol.* 72:8463-8471 (1998).

Dunbar, et al., "Retrovirally Marked CD34-Enriched Peripheral Blood and Bone Marrow Cells Contribute to Long-Term Engraftment After Autologous Transplantation," *Blood* 85(11):3048-3057 (1995).

Ellem, et al., "A Case Report: Immune Responses and Clinical Course of the First Human Use of Granulocyte/Macrophage-Colony-Stimulating-Factor-Transduced Autologous Melanoma Cells for Immunotherapy," *Cancer Immunol Immunother.* 44(1):10-20 (1997).

Fields, et al., "A Novel Genetic System to Detect Protein-Protein Interactions," *Nature* 340:245-246 (1989).

Follenzi, et al., "Gene Transfer by Lentiviral Vectors Is Limited by Nuclear Translocation and Rescued by HIV-1 POL Sequences," *Nature Genetics* 25:217-222 (2000).

Gao, et al., "Cationic Liposome-Mediated Gene Transfer," *Gene Therapy* 2:710-722 (1995).

Gribskov, et al., "Sigma Factors From *E. coli, B. subtilis*, Phage SP01 and Phage T4 are Homologous Proteins," *Nucl Acids Res.* 14(6):6745-6763 (1986).

Han, et al., "Ligand-Directed Retroviral Targeting of Human Breast Cancer Cells," *PNAS USA* 92:9747-9751 (1995).

Havranek, et al., "Automated Design of Specificity in Molecular Recognition," *Nat Struct Biol* 10-45-52 (2003).

Hermonat, et al., "Use of Adeno-Associated Virus As a Mammalian DNA Cloning Vector: Transduction of Neomycin Resistance Into Mammalian Tissue Culture Cells," *PNAS* 81:6466-6470 (1984).

Inaba, et al., "Generation of Large Numbers of Dendritic Cells From Mouse Bone Marrow Cultures Supplemented With Granulocyte/Macrophage Colony-Stimulating Factor," *J Exp Med* 176:1693-1702 (1992).

Jeggo, et al., "DNA Breakage and Repair," *Adv Genet* 38:185-218 (1998).

Johann, et al., "GLVRI, A Receptor for Gibbon Ape Leukemia Virus, Is Homologous to a Phosphate Permease of Neurospora Crassa and Is Expressed At High Levels in the Brain and Thymus," *J Virol* 66:1635-1640 (1992).

Kearns, et al., "Recombinant Adeno-Associated Virus (AAV-CFTR) Vectors Do Not Integrate in a Site-Specific Fashion in an Immortalized Epithelial Cell Line," *Gene Ther.* 9:748-755 (1996).

Kohn, et al., "Engraftment of Gene-Modified Umbilical Cord Blood Cells in Neonates With Adenosine Deaminase Deficiency," *Nat Med* 1:1017-1102 (1995).

Kotin, "Prospects for the Use of Adeno-Associated Virus As a Vector for Human Gene Therapy," *Hum. Gene Ther.* 5:793-801 (1994).

Kremer & Perricaudet, "Adenovirus and Adeno-Associated Virus Mediated Gene Transfer," *British Medical Bulletin* 51(1):31-44 (1995).

Malech, et al., "Prolonged Production of NADPH Oxidase-Corrected Granulocytes After Gene Therapy of Chronic Granulomatous Disease," *PNAS* 94(22):12133-12138 (1997).

Miller, et al., "Construction and Properties of Retrovirus Packaging Cells Based on Gibbon Ape Leukemia Virus," *J. Virol.* 65:2220-2224 (1991).

Miller, "Human Gene Therapy Comes of Age," *Nature* 357:455-460 (1992).

Miller, et al., "An Improved Zinc Finger Nuclease Architecture for Highly Specific Genome Editing," *Nature Biotechnology* 25(7):778-785 (2007).

Mitani & Caskey, "Delivering Therapeutic Genes—Matching Approach and Application," *TIBTECH* 11:162-166 (1993).

Muzyczka, "Adeno-Associated Virus (AAV) Vectors: Will They Work?" *J Clin Invest* 94:1351 (1994).

Nabel & Feigner, "Direct Gene Transfer for Immunotherapy and Immunization," *TIBTECH* 11:211-217 (1993).

Naldini, et al., "Efficient Transfer, Integration, and Sustained Long-Term Expression of the Transgene in Adult Rat Brains Injected With a Lentiviral Vector," *PNAS USA* 93:11382-11388 (1996).

Ni, et al., "Evaluation of Biodistribution and Safety of Adenovirus Vectors Containing Group B Fibers After Intravenous Injection Into Baboons," *Hum Gene Ther* 16:664-677 (2005).

Nilsson, et al., "Functionally Distinct Subpopulations of Cord Blood CD34+ Cells Are Transduced by Adenoviral Vectors With Serotype 5 or 35 Tropism," *Mol Ther* 9:377-388 (2004).

Nilsson, et al., "Development of an Adenoviral Vector System With Adenovirus Serotype 35 Tropism; Efficient Transient Gene Transfer Into Primary Malignant Hematopoietic Cells," *J. Gene Med* 6:631-641 (2004).

Nohaile, et al., "Altering Dimerization Specificity by Changes in Surface Electrostatics," *PNAS USA* 98:3109-3114 (2001).

O'Shea, et al., "Peptide 'Velcro': Design of a Heterodimeric Coiled Coil," *Curr Biol* 3:658-667 (1993).

Porteus, et al., "Chimeric Nucleases Stimulate Gene Targeting in Human Cells," *Science* 300:763 (2003).

Qiu, et al., "Mutation Detection Using Surveyor Nuclease," *Biotechniques* 36:702-707 (2004).

Rappold, et al., "Tumor Suppressor P53 Binding Protein 1 (53BP1) Is Involved in DNA Damage—Signaling Pathways," *J Cell Biol* 153:613-620 (2001).

Reddy, et al., "Development of Adenovirus Serotype 35 As a Gene Transfer Vector," *Virology* 311:384-393 (2003).

Remy, et al., "Gene Transfer With a Series of Lipophilic DNA-Binding Molecules," *Bioconjugate Chem* 5:647-654 (1994).

Rogakou, et al., "DNA Double-Stranded Breaks Induce Histone H2AX Phosphorylation on Serine 139," *J Biol Chem* 273:5858-5868 (1998).

Rogakou, et al., "Megabase Chromatin Domains Involved in DNA Double-Strand Breaks In Vivo," *J Cell Biol* 146:905-916 (1999).

Rosenecker, et al., "Adenovirus Infection in Cystic Fibrosis Patients: Implications for the Use of Adenoviral Vectors for Gene Transfer," *Infection* 24:5-8 (1996).

Samulski, et al., "Helper-Free Stocks of Recombinant Adeno-Associated Viruses: Normal Integration Does Not Require Viral Gene Expression," *J. Virol.* 63:3822-3828 (1989).

Schroers, et al., "Gene Transfer Into Human T Lymphocytes and Natural Killer Cells by AD5/F35 Chimeric Adenoviral Vectors," *Exp Hematol* 32:536-546 (2004).

Schultz, et al., "P53 Binding Protein 1 (53BP1) Is an Early Participant in the Cellular Response to DNA Double-Strand Breaks," *J Cell Biol* 151:1381-1390 (2000).

Shayakhmetov, et al., "Efficient Gene Transfer Into Human CD34+ Cells by a Retargeted Adenovirus Vector," *J Virol* 74:2567-2583 (2004).

Smith and Waterman, "Comparison of Biosequences," *Advances in Applied Mathematics* 2:482-489 (1981).
Sommerfelt, et al., "Receptor Interference Groups of 20 Retroviruses Plating on Human Cells," *Virol.* 176:58-59 (1990).
Sova, et al., "A Tumor-Targeted and Conditionally Replicating Oncolytic Adenovirus Vector Expressing Trail for Treatment of Liver Metastases," *Mol Ther* 9:496-509 (2004).
Sterman, et al., "Adenovirus-Mediated Herpes Simplex Virus Thymidine Kinase/Ganciclovir Gene Therapy in Patients With Localized Malignancy: Results of a Phase 1 Clinical Trial in Malignant Mesothelioma," *Hum. Gene Ther.* 7:1083-1089 (1998).
Stiff, et al., "ATM and DNA-PK Function Redundantly to Phosphorylate H2AX After Exposure to Ionizing Radiation," *Cancer Res* 64:2390-2396 (2004).
Szczepek, et al., "Structure-Based Redesign of the Dimerization Interface Reduces the Toxicity of Zinc-Finger Nucleases," *Nature Biotechnology* 25(7):786-793 (2007).
Szymczak, et al., "Correction of Multi-Gene Deficiency In Vivo Using a Single 'Self-Cleaving' 2A Peptide-Based Retroviral Vector," *Nat Biotechnol* 22:589-594 (2004).
Topf, et al., "Regional 'Pro-Drug' Gene Therapy: Intravenous Administration of an Adenoviral Vector Expressing the *E. coli* Cytosine Deaminase Gene and Systemic Administration of 5-Fluorocytosine Suppresses Growth of Hepatic Metastasis of Colon Carcinoma," *Gene Ther* 5:507-513 (1998).
Tratschin, et al., "Adeno-Associated Virus Vector for High-Frequency Integration, Expression, and Rescue of Genes in Mammalian Cells," *Mol. Cell. Biol.* 5:3251-3260 (1985).
Tratschin, et al., "A Human Parvovirus, Adeno-Associated Virus, As a Eucaryotic Vector: Transient Expression and Encapsidation of the Procaryotic Gene for Chloramphenicol Acetyltransferase," *Mol. Cell Biol.* 4:2072-2081 (1984).

Urnov, et al., "Highly Efficient Endogenous Human Gene Correction Using Designed Zinc-Finger Nucleases," *Nature* 435:646-651 (2005).
Van Brunt, "Molecular Farming: Transgenic Animals as Bioreactors," *Biotechnology* 6(10):1149-1154 (1988).
Vigne, et al., "Third-Generation Adenovectors for Gene Therapy," *Restorative Neurology and Neuroscience* 8:35-36 (1995).
Wagner, et al., "Efficient and Persistent Gene Transfer of AAV-CFTR in Maxillary Sinus," *Lancet* 351:1702-1703 (1998).
Wah, et al., "Structure of FokI Has Implications for DNA Cleavage," *PNAS USA* 95:10564-10569 (1998).
Welsh, et al., "Adenovirus-Mediated Gene Transfer for Cystic Fibrosis: Part A. Safety of Dose and Repeat Administration in the Nasal Epithelium. Part B. Clinical Efficacy in the Maxillary Sinus," *Hum. Gene Ther.* 2:205-218 (1995).
West, et al., "Gene Expression in Adeno-Associated Virus Vectors: The Effects of Chimeric MRNA Structure, Helper Virus, and Adenovirus VAI RNA," *Virology* 160:38-47 (1987).
Wilson, et al., "Formation of Infectious Hybrid Virions With Gibbon Ape Leukemia Virus and Human T-Cell Leukemia Virus Retroviral Envelope Glycoproteins and the GAG and POL Proteins of Moloney Murine Leukemia Virus," *J Virol* 63:2374-2378 (1989).
Yu, et al., "Progress Towards Gene Therapy for HIV Infection," *Gene Therapy* 1:13-26 (1994).
Zhu, et al., "Remodeling Domain Interfaces to Enhance Heterodimer Formation," *Protein Sci* 6:781-788 (1997).
Zufferey, et al., "Self-Inactivating Lentivirus Vector for Safe and Efficient In Vivo Gene Delivery," *J. Virol.* 72:9873-9880 (1998).

* cited by examiner

FIG. 1: Wild type FokI cleavage half domain
QLVKSELEEKKSELRHKLKYVPHEYIELIEIARNSTQDRILEMKVMEFFMKVYGYRGKH
LGGSRKPDGAIYTVGSPIDYGVIVDTKAYSGGYNLPIGQADEMQRYVEENQTRNKHINP
NEWWKVYPSSVTEFKFLFVSGHFKGNYKAQLTRLNHITNCNGAVLSVEELLIGGEMIKA
GTLTLEEVRRKFNNGEINF (SEQ ID NO:1)

FIG. 2A: Q486E:I499L dimerization mutant
QLVKSELEEKKSELRHKLKYVPHEYIELIEIARNSTQDRILEMKVMEFFMKVYGYRGKH
LGGSRKPDGAIYTVGSPIDYGVIVDTKAYSGGYNLPIGQADEMERYVEENQTRNKHLNP
NEWWKVYPSSVTEFKFLFVSGHFKGNYKAQLTRLNHITNCNGAVLSVEELLIGGEMIKA
GTLTLEEVRRKFNNGEINF (SEQ ID NO:2)

FIG. 2B: E490K:I538K dimerization mutant
QLVKSELEEKKSELRHKLKYVPHEYIELIEIARNSTQDRILEMKVMEFFMKVYGYRGKH
LGGSRKPDGAIYTVGSPIDYGVIVDTKAYSGGYNLPIGQADEMQRYVKENQTRNKHINP
NEWWKVYPSSVTEFKFLFVSGHFKGNYKAQLTRLNHKTNCNGAVLSVEELLIGGEMIKA
GTLTLEEVRRKFNNGEINF  (SEQ ID NO:3)

FIG. 3:
>wt FokI
361 ---------- ---------- ---QLVKSEL EEKKSELRHK LKYVPHEYIE LIEIARNSTQ
421 DRILEMKVME FFMKVYGYRG KHLGGSRKPD GAIYTVGSPI DYGVIVDTKA YSGGYNLPIG
481 QADEMQRYVE ENQTRNKHIN PNEWWKVYPS SVTEFKFLFV SGHFKGNYKA QLTRLNHITN
541 CNGAVLSVEE LLIGGEMIKA GTLTLEEVRR KFNNGEINF

>E490K
361 ---------- ---------- ---QLVKSEL EEKKSELRHK LKYVPHEYIE LIEIARNSTQ
421 DRILEMKVME FFMKVYGYRG KHLGGSRKPD GAIYTVGSPI DYGVIVDTKA YSGGYNLPIG
481 QADEMQRYVK ENQTRNKHIN PNEWWKVYPS SVTEFKFLFV SGHFKGNYKA QLTRLNHITN
541 CNGAVLSVEE LLIGGEMIKA GTLTLEEVRR KFNNGEINF

>Q486E
361 ---------- ---------- ---QLVKSEL EEKKSELRHK LKYVPHEYIE LIEIARNSTQ
421 DRILEMKVME FFMKVYGYRG KHLGGSRKPD GAIYTVGSPI DYGVIVDTKA YSGGYNLPIG
481 QADEMERYVE ENQTRNKHIN PNEWWKVYPS SVTEFKFLFV SGHFKGNYKA QLTRLNHITN
541 CNGAVLSVEE LLIGGEMIKA GTLTLEEVRR KFNNGEINF

>E490K:I538K ("plus" variant)
361 ---------- ---------- ---QLVKSEL EEKKSELRHK LKYVPHEYIE LIEIARNSTQ
421 DRILEMKVME FFMKVYGYRG KHLGGSRKPD GAIYTVGSPI DYGVIVDTKA YSGGYNLPIG
481 QADEMQRYVK ENQTRNKHIN PNEWWKVYPS SVTEFKFLFV SGHFKGNYKA QLTRLNHKTN
541 CNGAVLSVEE LLIGGEMIKA GTLTLEEVRR KFNNGEINF >Q486E:I499L ("minus" variant)
361 ---------- ---------- ---QLVKSEL EEKKSELRHK LKYVPHEYIE LIEIARNSTQ
421 DRILEMKVME FFMKVYGYRG KHLGGSRKPD GAIYTVGSPI DYGVIVDTKA YSGGYNLPIG
481 QADEMERYVE ENQTRNKHLN PNEWWKVYPS SVTEFKFLFV SGHFKGNYKA QLTRLNHITN
541 CNGAVLSVEE LLIGGEMIKA GTLTLEEVRR KFNNGEINF FIG. 6
a) 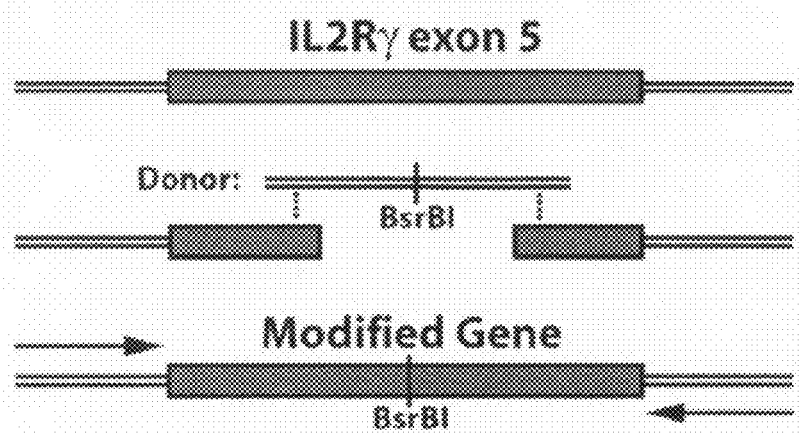
b) 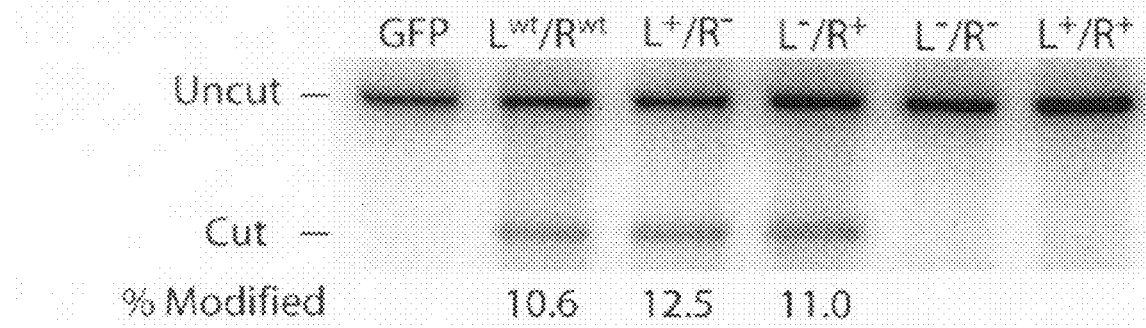

LR  TGTTCGGAGCCGCTTTAACCC▓▓▓▓▓▓▓▓▓▓TGCT
    ACAA▓▓▓▓▓▓▓▓▓▓TTGGGTGAGACACCTTCACGA

LL  TGTTCGGAGCCGCTTTAACCC▓▓▓▓▓▓▓▓▓▓TGCT
    ACAA▓▓▓▓▓▓▓▓▓▓TTGGGTTTCGCCGAGGCACGA

RR  TGTTCTTCCACAGAGTAACCC▓▓▓▓▓▓▓▓▓▓TGCT
    ACAA▓▓▓▓▓▓▓▓▓▓TTGGGTGAGACACCTTCACGA

B.

| ZFNs  | L^wt/R^wt |    |    | L⁻/R⁺ |    |    | L⁺/R⁻ |    |    |
|-------|-----------|----|----|-------|----|----|-------|----|----|
| Sites | LR        | LL | RR | LR    | LL | RR | LR    | LL | RR |
| Uncut |           |    |    |       |    |    |       |    |    |
| Cut   |           |    |    |       |    |    |       |    |    |
| %Cut  | 61        | 37 | 68 | 50    | 1.6| 1.4| 50    | 1.5| 3.1|

C.

| R | W | W | W | W | W | K | K | K | K | E | E | E | E | + | + | + | + | − | − | − | − |
|---|---|---|---|---|---|---|---|---|---|---|---|---|---|---|---|---|---|---|---|---|---|
| L | W | K | E | + | − | W | K | E | + | − | W | K | E | + | − | W | K | E | + | − | W | K | E | + | − |

Uncut —
Cut —

%Cut 100 100 72 73 40 100 96 94 9 96 64 97 19 32 3 76 9 33 0 45 55 98 13 52 0

SEQUENCE LISTING

```
<160> NUMBER OF SEQ ID NOS: 13

<210> SEQ ID NO 1
<211> LENGTH: 196
<212> TYPE: PRT
<213> ORGANISM: Planomicrobium okeanokoites

<400> SEQUENCE: 1

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 2
<211> LENGTH: 196
<212> TYPE: PRT
<213> ORGANISM: Artificial
<220> FEATURE:
<223> OTHER INFORMATION: engineered FokI cleavage half-domain with
      Q486E and I499L mutations
```

<400> SEQUENCE: 2

```
Gln Leu Val Lys Ser Glu Leu Glu Glu Lys Lys Ser Glu Leu Arg His
1               5                   10                  15
Lys Leu Lys Tyr Val Pro His Glu Tyr Ile Glu Leu Ile Glu Ile Ala
            20                  25                  30
Arg Asn Ser Thr Gln Asp Arg Ile Leu Glu Met Lys Val Met Glu Phe
        35                  40                  45
Phe Met Lys Val Tyr Gly Tyr Arg Gly Lys His Leu Gly Gly Ser Arg
50                  55                  60
Lys Pro Asp Gly Ala Ile Tyr Thr Val Gly Ser Pro Ile Asp Tyr Gly
65                  70                  75                  80
Val Ile Val Asp Thr Lys Ala Tyr Ser Gly Gly Tyr Asn Leu Pro Ile
                85                  90                  95
Gly Gln Ala Asp Glu Met Glu Arg Tyr Val Glu Glu Asn Gln Thr Arg
            100                 105                 110
Asn Lys His Leu Asn Pro Asn Glu Trp Trp Lys Val Tyr Pro Ser Ser
        115                 120                 125
Val Thr Glu Phe Lys Phe Leu Phe Val Ser Gly His Phe Lys Gly Asn
    130                 135                 140
Tyr Lys Ala Gln Leu Thr Arg Leu Asn His Ile Thr Asn Cys Asn Gly
145                 150                 155                 160
Ala Val Leu Ser Val Glu Glu Leu Leu Ile Gly Gly Glu Met Ile Lys
                165                 170                 175
Ala Gly Thr Leu Thr Leu Glu Glu Val Arg Arg Lys Phe Asn Asn Gly
            180                 185                 190
Glu Ile Asn Phe
        195
```

<210> SEQ ID NO 3
<211> LENGTH: 196
<212> TYPE: PRT
<213> ORGANISM: Artificial
<220> FEATURE:
<223> OTHER INFORMATION: engineered FokI cleavage half-domain with
      E490K and I538K mutations

<400> SEQUENCE: 3

```
Gln Leu Val Lys Ser Glu Leu Glu Glu Lys Lys Ser Glu Leu Arg His
1               5                   10                  15
Lys Leu Lys Tyr Val Pro His Glu Tyr Ile Glu Leu Ile Glu Ile Ala
            20                  25                  30
Arg Asn Ser Thr Gln Asp Arg Ile Leu Glu Met Lys Val Met Glu Phe
        35                  40                  45
Phe Met Lys Val Tyr Gly Tyr Arg Gly Lys His Leu Gly Gly Ser Arg
50                  55                  60
Lys Pro Asp Gly Ala Ile Tyr Thr Val Gly Ser Pro Ile Asp Tyr Gly
65                  70                  75                  80
Val Ile Val Asp Thr Lys Ala Tyr Ser Gly Gly Tyr Asn Leu Pro Ile
                85                  90                  95
Gly Gln Ala Asp Glu Met Gln Arg Tyr Val Lys Glu Asn Gln Thr Arg
            100                 105                 110
Asn Lys His Ile Asn Pro Asn Glu Trp Trp Lys Val Tyr Pro Ser Ser
        115                 120                 125
Val Thr Glu Phe Lys Phe Leu Phe Val Ser Gly His Phe Lys Gly Asn
    130                 135                 140
```

```
Tyr Lys Ala Gln Leu Thr Arg Leu Asn His Lys Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
                180                 185                 190

Glu Ile Asn Phe
        195

<210> SEQ ID NO 4
<211> LENGTH: 17
<212> TYPE: DNA
<213> ORGANISM: Artificial
<220> FEATURE:
<223> OTHER INFORMATION: primer

<400> SEQUENCE: 4
ggcgaggagc tgttcac                                                  17

<210> SEQ ID NO 5
<211> LENGTH: 17
<212> TYPE: DNA
<213> ORGANISM: Artificial
<220> FEATURE:
<223> OTHER INFORMATION: primer

<400> SEQUENCE: 5
tgcatacttc tgcctgc                                                  17

<210> SEQ ID NO 6
<211> LENGTH: 196
<212> TYPE: PRT
<213> ORGANISM: Artificial
<220> FEATURE:
<223> OTHER INFORMATION: engineered FokI cleavage half-domain with
      E490K mutation

<400> SEQUENCE: 6

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
                20                  25                  30

Arg Asn Ser Thr Gln Asp Arg Ile Leu Glu Met Lys Val Met Glu Phe
            35                  40                  45

Phe Met Lys Val Tyr Gly Tyr Arg Gly Lys His Leu Gly Gly Ser Arg
    50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Gln Arg Tyr Val Lys Glu Asn Gln Thr Arg
                100                 105                 110

Asn Lys His Ile Asn Pro Asn Glu Trp Trp Lys Val Tyr Pro Ser Ser
            115                 120                 125

Val Thr Glu Phe Lys Phe Leu Phe Val Ser Gly His Phe Lys Gly Asn
    130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175
```

```
Ala Gly Thr Leu Thr Leu Glu Glu Val Arg Arg Lys Phe Asn Asn Gly
            180                 185                 190

Glu Ile Asn Phe
        195

<210> SEQ ID NO 7
<211> LENGTH: 196
<212> TYPE: PRT
<213> ORGANISM: Artificial
<220> FEATURE:
<223> OTHER INFORMATION: engineered FokI cleavage half-domain with
      Q486E mutation

<400> SEQUENCE: 7

Gln Leu Val Lys Ser Glu Leu Glu Glu Lys Lys Ser Glu Leu Arg His
1               5                   10                  15

Lys Leu Lys Tyr Val Pro His Glu Tyr Ile Glu Leu Ile Glu Ile Ala
            20                  25                  30

Arg Asn Ser Thr Gln Asp Arg Ile Leu Glu Met Lys Val Met Glu Phe
        35                  40                  45

Phe Met Lys Val Tyr Gly Tyr Arg Gly Lys His Leu Gly Gly Ser Arg
50                  55                  60

Lys Pro Asp Gly Ala Ile Tyr Thr Val Gly Ser Pro Ile Asp Tyr Gly
65                  70                  75                  80

Val Ile Val Asp Thr Lys Ala Tyr Ser Gly Gly Tyr Asn Leu Pro Ile
                85                  90                  95

Gly Gln Ala Asp Glu Met Glu Arg Tyr Val Glu Glu Asn Gln Thr Arg
            100                 105                 110

Asn Lys His Ile Asn Pro Asn Glu Trp Trp Lys Val Tyr Pro Ser Ser
        115                 120                 125

Val Thr Glu Phe Lys Phe Leu Phe Val Ser Gly His Phe Lys Gly Asn
130                 135                 140

Tyr Lys Ala Gln Leu Thr Arg Leu Asn His Ile Thr Asn Cys Asn Gly
145                 150                 155                 160

Ala Val Leu Ser Val Glu Glu Leu Leu Ile Gly Gly Glu Met Ile Lys
                165                 170                 175

Ala Gly Thr Leu Thr Leu Glu Glu Val Arg Arg Lys Phe Asn Asn Gly
            180                 185                 190

Glu Ile Asn Phe
        195

<210> SEQ ID NO 8
<211> LENGTH: 37
<212> TYPE: DNA
<213> ORGANISM: Artificial
<220> FEATURE:
<223> OTHER INFORMATION: zinc finger target sequence in human IL-2
      receptor gamma gene

<400> SEQUENCE: 8
tgttcggagc cgctttaacc cactctgtgg aagtgct                        37

<210> SEQ ID NO 9
<211> LENGTH: 37
<212> TYPE: DNA
<213> ORGANISM: Artificial
<220> FEATURE:
<223> OTHER INFORMATION: zinc finger target sequence in human IL-2
      receptor gamma gene

<400> SEQUENCE: 9
```

```
<210> SEQ ID NO 10
<211> LENGTH: 37
<212> TYPE: DNA
<213> ORGANISM: Artificial
<220> FEATURE:
<223> OTHER INFORMATION: zinc finger target sequence in human IL-2
      receptor gamma gene

<400> SEQUENCE: 10
tgttcggagc cgctttaacc caaagcggct ccgtgct                              37

<210> SEQ ID NO 11
<211> LENGTH: 37
<212> TYPE: DNA
<213> ORGANISM: Artificial
<220> FEATURE:
<223> OTHER INFORMATION: zinc finger target sequence in human IL-2
      receptor gamma gene

<400> SEQUENCE: 11
acaagcctcg gcgaaattgg gtttcgccga ggcacga                              37

<210> SEQ ID NO 12
<211> LENGTH: 37
<212> TYPE: DNA
<213> ORGANISM: Artificial
<220> FEATURE:
<223> OTHER INFORMATION: zinc finger target sequence in human IL-2
      receptor gamma gene

<400> SEQUENCE: 12
tgttcttcca cagagtaacc cactctgtgg aagtgct                              37

<210> SEQ ID NO 13
<211> LENGTH: 37
<212> TYPE: DNA
<213> ORGANISM: Artificial
<220> FEATURE:
<223> OTHER INFORMATION: zinc finger target sequence in human IL-2
      receptor gamma gene

<400> SEQUENCE: 13
acaagaaggt gtctcattgg gtgagacacc ttcacga                              37
```

US 7,914,796 B2

ENGINEERED CLEAVAGE HALF-DOMAINS

CROSS-REFERENCE TO RELATED APPLICATIONS

This application is a continuation of U.S. patent application Ser. No. 11/805,850, filed May 23, 2007 now abandoned which claims the benefit of U.S. Provisional Application No. 60/808,486, filed May 25, 2006, which disclosures are hereby incorporated by reference in their entireties herein.

STATEMENT OF RIGHTS TO INVENTIONS MADE UNDER FEDERALLY SPONSORED RESEARCH

Not applicable.

TECHNICAL FIELD

The present disclosure is in the fields of polypeptide and genome engineering and homologous recombination.

BACKGROUND

Zinc finger nucleases (fusions of zinc finger domains and cleavage domains) for targeted cleavage of genomic DNA have been described. Such targeted cleavage events can be used, for example, to induce targeted mutagenesis, induce targeted deletions of cellular DNA sequences, and facilitate targeted recombination at a predetermined chromosomal locus. See, for example, United States Patent Publications 20030232410; 20050208489; 20050026157; 20050064474; 20060188987; 20060063231; and International Publication WO 07/014275, the disclosures of which are incorporated by reference in their entireties for all purposes.

To increase specificity, a pair of fusion proteins, each comprising a zinc finger binding domain and cleavage half-domain can be used to cleave the target genomic DNA. Because cleavage does not occur unless the cleavage half-domains associate to form a functional dimer, this arrangement increases specificity.

However, to further decrease off-target cleavage events, there remains a need for engineered cleavage half-domains that cleave DNA only upon formation of a heterodimer.

SUMMARY

The present disclosure provides engineered cleavage half-domains that form heterodimers with each other or with a wild-type cleavage half-domain. Also described are complexes (e.g., heterodimers) and fusion proteins comprising these engineered cleavage half-domains. The disclosure also provides methods of using these compositions for targeted cleavage of cellular chromatin in a region of interest and/or homologous recombination at a predetermined region of interest in cells.

Thus, in one aspect, described herein is an engineered cleavage half-domains, for example variants of FokI cleavage half-domains as shown in Table 1, FIG. 2 or FIG. 3. The engineered cleavage half-domain comprises one or more mutations as compared to the parental wild-type cleavage domain from which they are derived. In certain embodiments, the engineered cleavage half-domains are derived from FokI and comprise a mutation in one or more of amino acid residues 483, 486, 487, 490, 499, and/or 538, numbered relative to a wild-type FokI cleavage half-domain. In one embodiment, the engineered cleavage half-domain is derived from a wild-type FokI cleavage domain and comprises a mutation in amino acid residue 490, numbered relative to wild-type FokI. In another embodiment, the engineered cleavage half-domain comprises a mutation in amino acid residue 486, numbered relative to wild-type FokI.

The engineered cleavage half-domains described herein can form heterodimers with wild-type cleavage half-domains and/or with other engineered cleavage half-domains. In certain embodiments, the engineered cleavage half-domain comprises a mutation at position 490 (numbered relative to wild-type FokI), for instance a mutation that replaces the wild type Glu (E) residue with a Lys (K) and, optionally, a mutation at position 538, for instance Ile (I) to Lys (K) and forms a heterodimer with a wild-type FokI domain. In other embodiments, two engineered cleavage half-domains, one comprising a mutation at amino acid residues 490 and the other comprising a mutation at amino acid residue 486, are capable of forming a functional heterodimer. In another embodiment, the engineered cleavage half-domain comprises a mutation in amino acid residue 538, numbered relative to wild-type FokI and is capable of forming a functional heterodimer with an engineered cleavage half-domain comprising a mutation in amino acid residue 499 (numbered relative to wild-type FokI). In yet another embodiment, provided herein is an engineered cleavage half-domain comprising mutations in amino acid residues 490 and 538, numbered relative to wild-type FokI, which forms a functional heterodimer with an engineered cleavage half-domain comprising mutations in amino acid residues 486 and 499, numbered relative to wild-type FokI.

In another aspect, fusion polypeptides comprising a zinc finger binding domain (e.g., an engineered zinc finger binding domain) and an engineered cleavage half-domain as described herein are provided.

In another aspect, polynucleotides encoding any of the engineered cleavage half-domains or fusion proteins as described herein are provided.

In yet another aspect, cells comprising any of the polypeptides (e.g., fusion polypeptides) and/or polynucleotides as described herein are also provided. In one embodiment, the cells comprise a pair of fusion polypeptides, one fusion polypeptide comprising the cleavage half-domain shown in FIG. 2A and the other fusion polypeptide comprising the cleavage half-domain shown in FIG. 2B.

In yet another aspect, methods for targeted cleavage of cellular chromatin in a region of interest; methods of causing homologous recombination to occur in a cell; methods of treating infection; and/or methods of treating disease are provided. The methods involve cleaving cellular chromatin at a predetermined region of interest in cells by expressing a pair of fusion polypeptides as described herein (i.e., a pair of fusion polypeptides in which one fusion polypeptide comprises the engineered cleavage half-domains shown in FIG. 2A and the other fusion polypeptide comprises the engineered cleavage half-domain shown in FIG. 2B, which engineered cleavage half-domains form obligate heterodimers).

The engineered cleavage half domains described herein can be used in methods for targeted cleavage of cellular chromatin in a region of interest and/or homologous recombination at a predetermined region of interest in cells. Cells include cultured cells, cells in an organism and cells that have been removed from an organism for treatment in cases where the cells and/or their descendants will be returned to the organism after treatment. A region of interest in cellular chromatin can be, for example, a genomic sequence or portion thereof. Compositions include fusion polypeptides comprising an engineered zinc finger binding domain (e.g., a zinc finger binding domain having a novel specificity) and a cleavage half domain as described.

A fusion protein can be expressed in a cell, e.g., by delivering the fusion protein to the cell or by delivering a polynucleotide encoding the fusion protein to a cell, wherein the polynucleotide, if DNA, is transcribed, and an RNA molecule delivered to the cell or a transcript of a DNA molecule delivered to the cell is translated, to generate the fusion protein. Methods for polynucleotide and polypeptide delivery to cells are presented elsewhere in this disclosure.

Accordingly, in another aspect, a method for cleaving cellular chromatin in a region of interest can comprise (a) selecting a first sequence in the region of interest; (b) engineering a first zinc finger binding domain to bind to the first sequence; (c) expressing a first fusion protein in the cell, the first fusion protein comprising the first zinc finger binding domain and a first engineered cleavage half-domain as described herein; and (d) expressing a second fusion protein in the cell, the second fusion protein comprising a second zinc finger binding domain and a second cleavage half-domain as described herein, wherein the first fusion protein binds to the first sequence, and the second fusion protein binds to a second sequence located between 2 and 50 nucleotides from the first sequence, thereby positioning the engineered cleavage half-domains such that they form a heterodimer, which heterodimer cleaves cellular chromatin in the region of interest.

In other embodiments, any of the methods described herein may comprise (a) selecting first and second sequences in a region of interest, wherein the first and second sequences are between 2 and 50 nucleotides apart; (b) engineering a first zinc finger binding domain to bind to the first sequence; (c) engineering a second zinc finger binding domain to bind to the second sequence; (d) expressing a first fusion protein in the cell, the first fusion protein comprising the first engineered zinc finger binding domain and a first cleavage half-domain as described herein; (e) expressing a second fusion protein in the cell, the second fusion protein comprising the second engineered zinc finger binding domain and a second cleavage half-domain as described herein; wherein the first fusion protein binds to the first sequence and the second fusion protein binds to the second sequence, thereby positioning the first and second engineered cleavage half-domains such that they form a heterodimer which cleaves the cellular chromatin in the region of interest. In certain embodiments, cellular chromatin is cleaved at one or more sites between the first and second sequences to which the fusion proteins bind.

In further embodiments, a method for cleavage of cellular chromatin in a region of interest comprises (a) selecting the region of interest; (b) engineering a first zinc finger binding domain to bind to a first sequence in the region of interest; (c) providing a second zinc finger binding domain which binds to a second sequence in the region of interest, wherein the second sequence is located between 2 and 50 nucleotides from the first sequence; (d) expressing a first fusion protein in the cell, the first fusion protein comprising the first zinc finger binding domain and a first cleavage half-domain as described herein; and (e) expressing a second fusion protein in the cell, the second fusion protein comprising the second zinc finger binding domain and a second cleavage half domain as described herein; wherein the first fusion protein binds to the first sequence, and the second fusion protein binds to the second sequence, thereby positioning the first and second cleavage half-domains such that they form a heterodimer and the cellular chromatin is cleaved in the region of interest.

Also provided are methods of altering a region of cellular chromatin, for example to introduce targeted mutations. In certain embodiments, methods of altering cellular chromatin comprise introducing into the cell one or more targeted nucleases to create a double-stranded break in cellular chromatin at a predetermined site, and a donor polynucleotide, having homology to the nucleotide sequence of the cellular chromatin in the region of the break. Cellular DNA repair processes are activated by the presence of the double-stranded break and the donor polynucleotide is used as a template for repair of the break, resulting in the introduction of all or part of the nucleotide sequence of the donor into the cellular chromatin. Thus, a sequence in cellular chromatin can be altered and, in certain embodiments, can be converted into a sequence present in a donor polynucleotide.

Targeted alterations include, but are not limited to, point mutations (i.e., conversion of a single base pair to a different base pair), substitutions (i.e., conversion of a plurality of base pairs to a different sequence of identical length), insertions or one or more base pairs, deletions of one or more base pairs and any combination of the aforementioned sequence alterations.

The donor polynucleotide can be DNA or RNA, can be linear or circular, and can be single-stranded or double-stranded. It can be delivered to the cell as naked nucleic acid, as a complex with one or more delivery agents (e.g., liposomes, poloxamers) or contained in a viral delivery vehicle, such as, for example, an adenovirus or an adeno-associated Virus (AAV). Donor sequences can range in length from 10 to 1,000 nucleotides (or any integral value of nucleotides therebetween) or longer.

In certain embodiments, the frequency of homologous recombination can be enhanced by arresting the cells in the G2 phase of the cell cycle and/or by activating the expression of one or more molecules (protein, RNA) involved in homologous recombination and/or by inhibiting the expression or activity of proteins involved in non-homologous end-joining.

In any of the methods described herein, the second zinc finger binding domain may be engineered to bind to the second sequence.

Furthermore, in any of the methods described herein, the fusion proteins may be encoded by a single polynucleotide.

For any of the aforementioned methods, the cellular chromatin can be in a chromosome, episome or organellar genome. Cellular chromatin can be present in any type of cell including, but not limited to, prokaryotic and eukaryotic cells, fungal cells, plant cells, animal cells, mammalian cells, primate cells and human cells. In addition, in any of the methods described herein, at least one zinc finger binding domain is engineered, for example by design or selection methods.

BRIEF DESCRIPTION OF THE DRAWINGS

FIG. 1 shows the amino acid sequence of the wild-type FokI cleavage half-domain (SEQ ID NO:1). Positions at which the sequence can be altered (483, 486, 487, 490, 499 and 538) to form engineered cleavage half-domains are bolded and underlined.

FIG. 2, panels A and B, show the amino acid sequence of exemplary engineered cleavage half-domains as described herein. FIG. 2A (SEQ ID NO:2) shows sequence of a mutant cleavage half-domain that forms a heterodimer with the engineered cleavage half-domain shown in FIG. 2B. Positions at which the sequence was altered as compared to wild-type (corresponding to amino acid residues 486 and 499) are underlined. FIG. 2B shows the amino acid sequence of another exemplary engineered cleavage half-domain (SEQ ID NO:3) that can be used in the zinc finger nucleases (ZFNs) described herein. Positions at which the sequence was altered as compared to wild-type (corresponding to amino acid residues 490 and 538) are underlined.

FIG. 3 shows amino acid sequence of various FokI cleavage domains, including wild-type (SEQ ID NO:1), E490K (SEQ ID NO:6), Q486E (SEQ ID NO:7), E490K:I538K (SEQ ID NO:3) and Q486E:I499L (SEQ ID NO:2). Positions 486, 490, 499, and 538 are underlined in each sequence. Differences relative to wild-type are boxed.

FIG. 4, panels A to C, depict exemplary ZFNs comprising a zinc finger binding domain and a cleavage half-domain.

FIG. 5A is a schematic depicting the reporter system used to screen cleavage domain variants for gene correction activity. The system utilizes an HEK293 cell line that contains an integrated copy of the eGFP gene interrupted by a short DNA fragment bearing the cleavage target for a well-characterized ZFN dimer (top line). The ZFN dimer is described in Urnov et al. (2005) Nature 435:646-651. Cleavage and resection yields a substrate for homology directed repair (HDR), which may be templated from an exogenous donor DNA fragment bearing a portion of the eGFP sequence (middle and bottom). Gene correction efficiency is monitored via counting the fraction of cells that convert to green fluorescence. The dashed line between the inactive eGFP gene and the donor indicates the HDR process.

FIG. 5B shows flow cytometry data for reporter cells transfected with either the donor only or the donor plus ZFNs. The fraction of GFP positive cells may be quantified using the indicated gate.

FIG. 5C is a schematic depicting the central region of the dimer interface of wild-type FokI. Residues mutated are labeled with the amino acid and position.

FIG. 5D depicts the iterative screening process used to identify FokI cleavage domain variants that function as obligate heterodimers. "Wt" indicates the wild-type FokI cleavage domain. FokI cleavage domain variants are indicated via mutations relative to the wild-type sequence using the single-letter amino acid code (E=Glu; K=Lys; I=Ile; Q=Gln; L=Leu). In each development step, curved arrows connect the parental cleavage domain to the discovered variant having the best heterodimerization properties. The arrows also highlight the strategy of alternately modifying each surface of the dimer interface in a stepwise fashion. The relative gene correction rates indicate the fraction of GFP-positive cells observed for the indicated complex normalized to the fraction of GFP-positive cells obtained with the wt/wt dimer. The % gene correction achieved with the wt/wt dimer was 1.27±0.11 in the experiment yielding data highlighted with an asterisk and 0.93±0.09 in the experiment yielding the rest of the data.

FIG. 5E is a schematic depicting a model of the interface between the "+" and "−" cleavage domain heterodimer variants. Introduced mutations are boxed.

FIG. 5F is a graph depicting gene correction efficiencies of the "+" and "−" cleavage domain variants in the GFP reporter system. "Lwt" denotes the "left" ZFP fused to a wild-type FokI cleavage domain (identical to ZFN-L* of Urnov et al., supra) while L+ and L− denote the "left" ZFP fused to "+" and "−" cleavage domain variants. Similarly, Rwt denotes the "right" ZFP fused to a wild-type FokI cleavage domain5 while R+ and R− denote the "right" ZFP fused to the "+" and "−" cleavage domain variants. "D.O." denotes cells treated with donor plasmid only. The variants stimulate efficient gene correction as heterodimers (compare L+/R− and L−/R+ vs. Lwt/Rwt) but not when forced to self-associate (L+/R+ and L−/R−). Values represent the average of four independent transfections. Error bars denote standard deviations.

FIG. 6, panels A and B, depict gene correction activity of FokI cleavage domain variants at an endogenous target. FIG. 6A is a schematic depicting endogenous gene correction assay. Cleavage and resection of the native IL2Rγ gene (top and middle) yields a substrate for HDR which may be templated using a donor DNA fragment bearing a restriction site for BsrBI (middle and bottom). Gene correction efficiency is then quantified via PCR-amplification of the endogenous locus using primers that bind outside of the donor sequence followed by digestion of the PCR product with BsrBI. The dashed line between the resected IL2Rγ gene and donor indicates the HDR process. FIG. 6B shows results of the endogenous gene correction assay on human K562 cells transfected with the indicated constructs. "GFP" indicates pmaxGFP (Amaxa), while other construct identities are as described in FIG. 5F. "Uncut" indicates the position of undigested PCR product and "cut" indicates the position of the fragments created by BsrBI digestion (which appear only if the donor site has been transferred from the donor to the gene). The numbers below the lanes with visible BsrBI bands indicate the percentage of cleaved PCR product.

FIG. 7, panels A and B, depict preferential heterodimer activity of FokI variants as demonstrated via DNA cleavage in vitro. FIG. 7A depicts both DNA strands of the target fragments (top strand shown in 5' to 3' orientation and the bottom strand written 3' to 5' orientation). The primary strand of the 12 bp sites for the left (L) and right (R) ZFN pairs are boxed and shaded. FIG. 7B shows in vitro target cleavage by the indicated ZFN combinations. Migration of cleaved and uncleaved products is indicated. Numbers below each lane indicate the percentage of DNA in cleaved bands. The protein concentration of the Lwt/Rwt combination was adjusted to yield levels of LR target cleavage similar to that of the L+/R− and L−/R+ combinations. While homodimer formation can occur with the wild-type nuclease domain to cleave the three targets by the Lwt/Rwt combination (left panel), little or no cleavage of the LL and RR targets is exhibited by ZFNs bearing the heterodimer cleavage domain variants (center and right panels). FIG. 7C depicts results of 25 DNA cleavage experiments run under the same experimental conditions as for FIGS. 7A and B (Example 5), except that the full concentration of each left and right nuclease was used and the "LR" site was used for all samples. "R" indicates the type of cleavage domain on the R nuclease and "L" indicates the type of cleavage domain on the L nuclease. W=wild-type; K=E490K; E=Q486E: "+"=E490K:I538K; "−"=Q486E: I499L. "Uncut" indicates the location of the uncut target DNA and "cut" indicates the location of the cut target DNA. The percent DNA cleaved was calculated for each sample and is indicates below each lane.

DETAILED DESCRIPTION

Figure 4A:
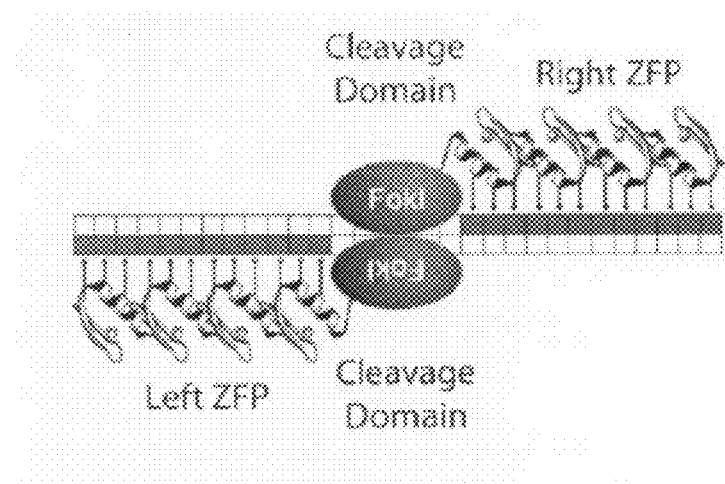
FIG. 4A depicts a ZFN dimer bound to a typical, nonpalindromic DNA target. Each ZFN consists of the cleavage domain of FokI fused to a zinc finger protein (ZFP) that has been customized to specifically recognize either a "left" or "right" half-site, which are separated by a spacer of either 5 or 6 bp. Binding of both ZFNs allows dimerization of the FokI nuclease domains and DNA cleavage. The exemplary ZFN dimers are depicted with four fingers that each bind 12 base pair sites.
Figure 4B:
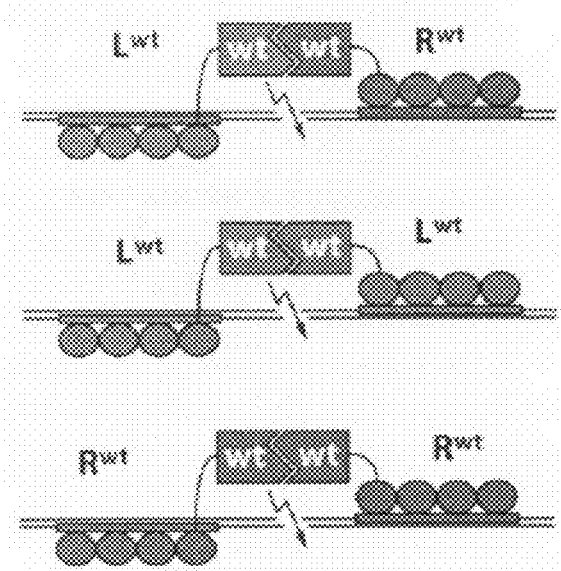
FIG. 4B depicts how coexpression of ZFNs with wild-type cleavage half domains results in both heterodimer (top line) and homodimer (middle and bottom lines) formation. "Lwt" refers to left ZFP fused to the wild-type FokI cleavage domain and "Rwt" refers to right ZFP fused to wild-type FokI cleavage domain). ZFP domains are indicated by four adjacent circles and cleavage half-domains are depicted by complementary polygons labeled "wt." Jagged arrows highlight the capacity of each dimer species to cleave DNA.
Figure 4C:
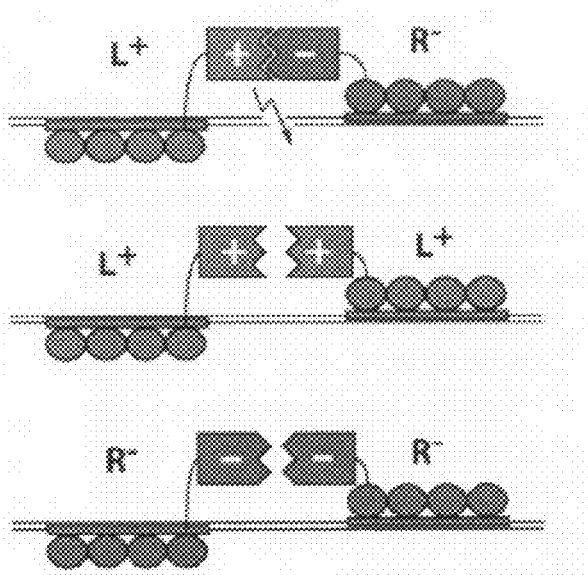
FIG. 4C depicts how coexpression of ZFNs with engineered cleavage half-domains as described herein results in only heterodimer formation (top line) and eliminates off-target activity by homodimer species (middle and bottom lines). The labels L+ and R− denote, respectively, the "left" and "right" ZFPs fused to the variant cleavage domains. The absence of a jagged arrow with the L+/L+ and R−/R− pairings denotes the inability of these homodimers to cleave DNA.

Disclosed herein are engineered cleavage half-domains and fusion polypeptides comprising these engineered cleavage half-domains useful for targeted cleavage of cellular chromatin and for targeted alteration of a cellular nucleotide sequence, e.g., by targeted cleavage followed by non-homologous end joining or by targeted cleavage followed by homologous recombination between an exogenous polynucleotide (comprising one or more regions of homology with the cellular nucleotide sequence) and a genomic sequence.

Exemplary engineered cleavage half-domains are shown in Table 1 as well as FIGS. 2 and 3. The variants in FIG. 2 include two mutations such that they form heterodimers with each other, but not homodimers. This increases the specificity of DNA cleavage and/or increases the concentration of the intended complex (by reducing or eliminating competition from homodimers). When incorporated into zinc finger nuclease fusion proteins, these variants induce gene modification at the intended target (both at an endogenous locus and when tested using an integrated GFP reporter assay) while significantly reducing genome wide DNA cleavage as compared to wild-type cleavage half-domains.

Thus, the engineered cleavage half-domains described herein significantly impair homodimer function, since forcing two copies of the same variant to interact reduces or abolishes gene modification. Reduced homodimer function provides improved ZFN cleavage specificity in vivo, without any decrease in either ZFN expression or the ability to stimulate modification of the desired target site.

General

Practice of the methods, as well as preparation and use of the compositions disclosed herein employ, unless otherwise indicated, conventional techniques in molecular biology, biochemistry, chromatin structure and analysis, computational chemistry, cell culture, recombinant DNA and related fields as are within the skill of the art. These techniques are fully explained in the literature. See, for example, Sambrook et al. MOLECULAR CLONING: A LABORATORY MANUAL, Second edition, Cold Spring Harbor Laboratory Press, 1989 and Third edition, 2001; Ausubel et al., CURRENT PROTOCOLS IN MOLECULAR BIOLOGY, John Wiley & Sons, New York, 1987 and periodic updates; the series METHODS IN ENZYMOLOGY, Academic Press, San Diego; Wolffe, CHROMATIN STRUCTURE AND FUNCTION, Third edition, Academic Press, San Diego, 1998; METHODS IN ENZYMOLOGY, Vol. 304, "Chromatin" (P. M. Wassarman and A. P. Wolffe, eds.), Academic Press, San Diego, 1999; and METHODS IN MOLECULAR BIOLOGY, Vol. 119, "Chromatin Protocols" (P. B. Becker, ed.) Humana Press, Totowa, 1999.

Definitions

The terms "nucleic acid," "polynucleotide," and "oligonucleotide" are used interchangeably and refer to a deoxyribonucleotide or ribonucleotide polymer, in linear or circular conformation, and in either single- or double-stranded form. For the purposes of the present disclosure, these terms are not to be construed as limiting with respect to the length of a polymer. The terms can encompass known analogues of natural nucleotides, as well as nucleotides that are modified in the base, sugar and/or phosphate moieties (e.g., phosphorothioate backbones). In general, an analogue of a particular nucleotide has the same base-pairing specificity; i.e., an analogue of A will base-pair with T.

The terms "polypeptide," "peptide" and "protein" are used interchangeably to refer to a polymer of amino acid residues. The term also applies to amino acid polymers in which one or more amino acids are chemical analogues or modified derivatives of a corresponding naturally-occurring amino acids.

"Binding" refers to a sequence-specific, non-covalent interaction between macromolecules (e.g., between a protein and a nucleic acid). Not all components of a binding interaction need be sequence-specific (e.g., contacts with phosphate residues in a DNA backbone), as long as the interaction as a whole is sequence-specific. Such interactions are generally characterized by a dissociation constant ($K_d$) of $10^{-6}$ $M^{-1}$ or lower. "Affinity" refers to the strength of binding: increased binding affinity being correlated with a lower $K_d$.

A "binding protein" is a protein that is able to bind non-covalently to another molecule. A binding protein can bind to, for example, a DNA molecule (a DNA-binding protein), an RNA molecule (an RNA-binding protein) and/or a protein molecule (a protein-binding protein). In the case of a protein-binding protein, it can bind to itself (to form homodimers, homotrimers, etc.) and/or it can bind to one or more molecules of a different protein or proteins. A binding protein can have more than one type of binding activity. For example, zinc finger proteins have DNA-binding, RNA-binding and protein-binding activity.

A "zinc finger DNA binding protein" (or binding domain) is a protein, or a domain within a larger protein, that binds DNA in a sequence-specific-manner through one or more zinc fingers, which are regions of amino acid sequence within the binding domain whose structure is stabilized through coordination of a zinc ion. The term zinc finger DNA binding protein is often abbreviated as zinc finger protein or ZFP.

Zinc finger binding domains can be "engineered" to bind to a predetermined nucleotide sequence. Non-limiting examples of methods for engineering zinc finger proteins are design and selection. A designed zinc finger- protein is a protein not occurring in nature whose design/composition results principally from rational criteria. Rational criteria for design include application of substitution rules and computerized algorithms for processing information in a database storing information of existing ZFP designs and binding data. See, for example, U.S. Pat. Nos. 6,140,081; 6,453,242; and 6,534,261; see also WO 98/53058; WO 98/53059; WO 98/53060; WO 02/016536 and WO 03/016496.

A "selected" zinc finger protein is a protein not found in nature whose production results primarily from an empirical process such as phage display, interaction trap or hybrid selection. See e.g., U.S. Pat. Nos. 5,789,538; 5,925,523; 6,007,988; 6,013,453; 6,200,759; WO 95/19431; WO 96/06166; WO 98/53057; WO 98/54311; WO 00/27878; WO 01/60970 WO 01/88197 and WO 02/099084.

The term "sequence" refers to a nucleotide sequence of any length, which can be DNA or RNA; can be linear, circular or branched and can be either single-stranded or double stranded. The term "donor sequence" refers to a nucleotide sequence that is inserted into a genome. A donor sequence can be of any length, for example between 2 and 10,000 nucleotides in length (or any integer value therebetween or thereabove), preferably between about 100 and 1,000 nucleotides in length (or any integer therebetween), more preferably between about 200 and 500 nucleotides in length.

A "homologous, non-identical sequence" refers to a first sequence which shares a degree of sequence identity with a second sequence, but whose sequence is not identical to that of the second sequence. For example, a polynucleotide comprising the wild-type sequence of a mutant gene is homologous and non-identical to the sequence of the mutant gene. In certain embodiments, the degree of homology between the two sequences is sufficient to allow homologous recombination therebetween, utilizing normal cellular mechanisms. Two homologous non-identical sequences can be any length and their degree of non-homology can be as small as a single nucleotide (e.g., for correction of a genomic point mutation by targeted homologous recombination) or as large as 10 or more kilobases (e.g., for insertion of a gene at a predetermined ectopic site in a chromosome). Two polynucleotides comprising the homologous non-identical sequences need not be the same length. For example, an exogenous polynucleotide (i.e., donor polynucleotide) of between 20 and 10,000 nucleotides or nucleotide pairs can be used.

Techniques for determining nucleic acid and amino acid sequence identity are known in the art. Typically, such techniques include determining the nucleotide sequence of the mRNA for a gene and/or determining the amino acid sequence encoded thereby, and comparing these sequences to a second nucleotide or amino acid sequence. Genomic sequences can also be determined and compared in this fashion. In general, identity refers to an exact nucleotide-to-nucleotide or amino acid-to-amino acid correspondence of two polynucleotides or polypeptide sequences, respectively. Two or more sequences (polynucleotide or amino acid) can be compared by determining their percent identity. The percent identity of two sequences, whether nucleic acid or amino acid sequences, is the number of exact matches between two aligned sequences divided by the length of the shorter sequences and multiplied by 100. An approximate alignment for nucleic acid sequences is provided by the local homology algorithm of Smith and Waterman, *Advances in Applied Mathematics* 2:482-489 (1981). This algorithm can be applied to amino acid sequences by using the scoring matrix developed by Dayhoff, *Atlas of Protein Sequences and Structure*, M. O. Dayhoff ed., 5 suppl. 3:353-358, National Biomedical Research Foundation, Washington, D.C., USA, and normalized by Gribskov, *Nucl. Acids Res.* 14(6):6745-6763 (1986). An exemplary implementation of this algorithm to determine percent identity of a sequence is provided by the Genetics Computer Group (Madison, Wis.) in the "BestFit" utility application. The default parameters for this method are described in the Wisconsin Sequence Analysis Package Program Manual, Version 8 (1995) (available from Genetics Computer Group, Madison, Wis.). A preferred method of establishing percent identity in the context of the present disclosure is to use the MPSRCH package of programs copyrighted by the University of Edinburgh, developed by John F. Collins and Shane S. Sturrok, and distributed by IntelliGenetics, Inc. (Mountain View, Calif.). From this suite of packages the Smith-Waterman algorithm can be employed where default parameters are used for the scoring table (for example, gap open penalty of 12, gap extension penalty of one, and a gap of six). From the data generated the "Match" value reflects sequence identity. Other suitable programs for calculating the percent identity or similarity between sequences are generally known in the art, for example, another alignment program is BLAST, used with default parameters. For example, BLASTN and BLASTP can be used using the following default parameters: genetic code=standard; filter=none; strand=both; cutoff=60; expect=10; Matrix=BLOSUM62; Descriptions=50 sequences; sort by=HIGH SCORE; Databases=non-redundant, GenBank+ EMBL+DDBJ+PDB+GenBank CDS translations+Swiss protein+Spupdate+PIR. Details of these programs can be found at the following internet address: http://www.ncbi.nlm.nih.gov/cgi-bin/BLAST. With respect to sequences described herein, the range of desired degrees of sequence identity is approximately 80% to 100% and any integer value therebetween. Typically the percent identities between sequences are at least 70-75%, preferably 80-82%, more preferably 85-90%, even more preferably 92%, still more preferably 95%, and most preferably 98% sequence identity.

Alternatively, the degree of sequence similarity between polynucleotides can be determined by hybridization of polynucleotides under conditions that allow formation of stable duplexes between homologous regions, followed by digestion with single-stranded-specific nuclease(s), and size determination of the digested fragments. Two nucleic acid, or two polypeptide sequences are substantially homologous to each other when the sequences exhibit at least about 70%-75%, preferably 80%-82%, more preferably 85%-90%, even more preferably 92%, still more preferably 95%, and most preferably 98% sequence identity over a defined length of the molecules, as determined using the methods above. As used herein, substantially homologous also refers to sequences showing complete identity to a specified DNA or polypeptide sequence. DNA sequences that are substantially homologous can be identified in a Southern hybridization experiment under; for example, stringent conditions, as defined for that particular system. Defining appropriate hybridization conditions is within the skill of the art. See, e.g., Sambrook et al., supra; *Nucleic Acid Hybridization: A Practical Approach*, editors B. D. Hames and S. J. Higgins, (1985) Oxford; Washington, D.C.; IRL Press).

Selective hybridization of two nucleic acid fragments can be determined as follows. The degree of sequence identity between two nucleic acid molecules affects the efficiency and strength of hybridization events between such molecules. A partially identical nucleic acid sequence will at least partially inhibit the hybridization of a completely identical sequence to a target molecule. Inhibition of hybridization of the completely identical sequence can be assessed using hybridization assays that are well known in the art (e.g., Southern (DNA) blot, Northern (RNA) blot, solution hybridization, or the like, see Sambrook, et al., *Molecular Cloning: A Laboratory Manual*, Second Edition, (1989) Cold Spring Harbor, N.Y.). Such assays can be conducted using varying degrees of selectivity, for example, using conditions varying from low to high stringency. If conditions of low stringency are employed, the absence of non-specific binding can be assessed using a secondary probe that lacks even a partial degree of sequence identity (for example, a probe having less than about 30% sequence identity with the target molecule), such that, in the absence of non-specific binding events, the secondary probe will not hybridize to the target.

When utilizing a hybridization-based detection system, a nucleic acid probe is chosen that is complementary to a reference nucleic acid sequence, and then by selection of appropriate conditions the probe and the reference sequence selectively hybridize, or bind, to each other to form a duplex molecule. A nucleic acid molecule that is capable of hybridizing selectively to a reference sequence under moderately stringent hybridization conditions typically hybridizes under conditions that allow detection of a target nucleic acid sequence of at least about 10-14 nucleotides in length having at least approximately 70% sequence identity with the sequence of the selected nucleic acid probe. Stringent hybridization conditions typically allow detection of target nucleic acid sequences of at least about 10-14 nucleotides in length having a sequence identity of greater than about 90-95% with the sequence of the selected nucleic acid probe. Hybridization conditions useful for probe/reference sequence hybridization, where the probe and reference sequence have a specific degree of sequence identity, can be determined as is known in the art (see, for example, *Nucleic Acid Hybridization: A Practical Approach*, editors B. D. Hames and S. J. Higgins, (1985) Oxford; Washington, D.C.; IRL Press).

Conditions for hybridization are well-known to those of skill in the art. Hybridization stringency refers to the degree to which hybridization conditions disfavor the formation of hybrids containing mismatched nucleotides, with higher stringency correlated with a lower tolerance for mismatched hybrids. Factors that affect the stringency of hybridization are well-known to those of skill in the art and include, but are not limited to, temperature, pH, ionic strength, and concentration of organic solvents such as, for example, formamide and dimethylsulfoxide. As is known to those of skill in the art, hybridization stringency is increased by higher temperatures, lower ionic strength and lower solvent concentrations.

With respect to stringency conditions for hybridization, it is well known in the art that numerous equivalent conditions can be employed to establish a particular stringency by varying, for example, the following factors: the length and nature of the sequences, base composition of the various sequences, concentrations of salts and other hybridization solution components, the presence or absence of blocking agents in the hybridization solutions (e.g., dextran sulfate, and polyethylene glycol), hybridization reaction temperature and time parameters, as well as, varying wash conditions. The selection of a particular set of hybridization conditions is selected following standard methods in the art (see, for example, Sambrook, et al., *Molecular Cloning: A Laboratory Manual*, Second Edition, (1989) Cold Spring Harbor, N.Y.).

"Recombination" refers to a process of exchange of genetic information between two polynucleotides. For the purposes of this disclosure, "homologous recombination (HR)" refers to the specialized form of such exchange that takes place, for example, during repair of double-strand breaks in cells. This process requires nucleotide sequence homology, uses a "donor" molecule to template repair of a "target" molecule (i.e., the one that experienced the double-strand break), and is variously known as "non-crossover gene conversion" or "short tract gene conversion," because it leads to the transfer of genetic information from the donor to the target. Without wishing to be bound by any particular theory, such transfer can involve mismatch correction of heteroduplex DNA that forms between the broken target and the donor, and/or "synthesis-dependent strand annealing," in which the donor is used to resynthesize genetic information that will become part of the target, and/or related processes. Such specialized HR often results in an alteration of the sequence of the target molecule such that part or all of the sequence of the donor polynucleotide is incorporated into the target polynucleotide.

"Cleavage" refers to the breakage of the covalent backbone of a DNA molecule. Cleavage can be initiated by a variety of methods including, but not limited to, enzymatic or chemical hydrolysis of a phosphodiester bond. Both single-stranded cleavage and double-stranded cleavage are possible, and double-stranded cleavage can occur as a result of two distinct single-stranded cleavage events. DNA cleavage can result in the production of either blunt ends or staggered ends. In certain embodiments, fusion polypeptides are used for targeted double-stranded DNA cleavage.

An "cleavage half-domain" is a polypeptide sequence which, in conjunction with a second polypeptide (either identical or different) forms a complex having cleavage activity (preferably double-strand cleavage activity). The terms "first and second cleavage half-domains;" "+ and − cleavage half-domains" and "right and left cleavage half-domains" are used interchangeably to refer to pairs of cleavage half-domains that dimerize.

An "engineered cleavage half-domain" is a cleavage half-domain that has been modified so as to form obligate heterodimers with another cleavage half-domain (e.g., another engineered cleavage half-domain).

"Chromatin" is the nucleoprotein structure comprising the cellular genome. Cellular chromatin comprises nucleic acid, primarily DNA, and protein, including histones and non-histone chromosomal proteins. The majority of eukaryotic cellular chromatin exists in the form of nucleosomes, wherein a nucleosome core comprises approximately 150 base pairs of DNA associated with an octamer comprising two each of histones H2A, H2B, H3 and H4; and linker DNA (of variable length depending on the organism) extends between nucleosome cores. A molecule of histone H1 is generally associated with the linker DNA. For the purposes of the present disclosure, the term "chromatin" is meant to encompass all types of cellular nucleoprotein, both prokaryotic and eukaryotic. Cellular chromatin includes both chromosomal and episomal chromatin.

A "chromosome," is a chromatin complex comprising all or a portion of the genome of a cell. The genome of a cell is often characterized by its karyotype, which is the collection of all the chromosomes that comprise the genome of the cell. The genome of a cell can comprise one or more chromosomes.

An "episome" is a replicating nucleic acid, nucleoprotein complex or other structure comprising a nucleic acid that is not part of the chromosomal karyotype of a cell. Examples of episomes include plasmids and certain viral genomes.

An "accessible region" is a site in cellular chromatin in which a target site present in the nucleic acid can be bound by an exogenous molecule which recognizes the target site. Without wishing to be bound by any particular theory, it is believed that an accessible region is one that is not packaged into a nucleosomal structure. The distinct structure of an accessible region can often be detected by its sensitivity to chemical and enzymatic probes, for example, nucleases.

A "target site" or "target sequence" is a nucleic acid sequence that defines a portion of a nucleic acid to which a binding molecule will bind, provided sufficient conditions for binding exist. For example, the sequence 5'-GAATTC-3' is a target site for the Eco RI restriction endonuclease.

An "exogenous" molecule is a molecule that is not normally present in a cell, but can be introduced into a cell by one or more genetic, biochemical or other methods. "Normal presence in the cell" is determined with respect to the particular developmental stage and environmental conditions of the cell. Thus, for example, a molecule that is present only during embryonic development of muscle is an exogenous molecule with respect to an adult muscle cell. Similarly, a molecule induced by heat shock is an exogenous molecule with respect to a non-heat-shocked cell. An exogenous molecule can comprise, for example, a functioning version of a malfunctioning endogenous molecule or a malfunctioning version of a normally-functioning endogenous molecule.

An exogenous molecule can be, among other things, a small molecule, such as is generated by a combinatorial chemistry process, or a macromolecule such as a protein, nucleic acid, carbohydrate, lipid, glycoprotein, lipoprotein, polysaccharide, any modified derivative of the above molecules, or any complex comprising one or more of the above molecules. Nucleic acids include DNA and RNA, can be single- or double-stranded; can be linear, branched or circular; and can be of any length. Nucleic acids include those capable of forming duplexes, as well as triplex-forming nucleic acids. See, for example, U.S. Pat. Nos. 5,176,996 and 5,422,251. Proteins include, but are not limited to, DNA-binding proteins, transcription factors, chromatin remodeling factors, methylated DNA binding proteins, polymerases, methylases, demethylases, acetylases, deacetylases, kinases, phosphatases, integrases, recombinases, ligases, topoisomerases, gyrases and helicases.

An exogenous molecule can be the same type of molecule as an endogenous molecule, e.g., an exogenous protein or nucleic acid. For example, an exogenous nucleic acid can comprise an infecting viral genome, a plasmid or episome introduced into a cell, or a chromosome that is not normally present in the cell. Methods for the introduction of exogenous molecules into cells are known to those of skill in the art and include, but are not limited to, lipid-mediated transfer (i.e., liposormes, including neutral and cationic lipids), electroporation, direct injection, cell fusion, particle bombardment, calcium phosphate co-precipitation, DEAE-dextran-mediated transfer and viral vector-mediated transfer.

By contrast, an "endogenous" molecule is one that is normally present in a particular cell at a particular developmental stage under particular environmental conditions. For example, an endogenous nucleic acid can comprise a chromosome, the genome of a mitochondrion, chloroplast or other organelle, or a naturally-occurring episomal nucleic acid. Additional endogenous molecules can include proteins, for example, transcription factors and enzymes.

A "fusion" molecule is a molecule in which two or more subunit molecules are linked, preferably covalently. The subunit molecules can be the same chemical type of molecule, or can be different chemical types of molecules. Examples of the first type of fusion molecule include, but are not limited to, fusion proteins (for example, a fusion between a ZFP DNA-binding domain and a cleavage domain) and fusion nucleic acids (for example, a nucleic acid encoding the fusion protein described supra). Examples of the second type of fusion molecule include, but are not limited to, a fusion between a triplex-forming nucleic acid and a polypeptide, and a fusion between a minor groove binder and a nucleic acid.

Expression of a fusion protein in a cell can result from delivery of the fusion protein to the cell or by delivery of a polynucleotide encoding the fusion protein to a cell, wherein the polynucleotide is transcribed, and the transcript is translated, to generate the fusion protein. Trans-splicing, polypeptide cleavage and polypeptide ligation can also be involved in expression of a protein in a cell. Methods for polynucleotide and polypeptide delivery to cells are presented elsewhere in this disclosure.

A "gene," for the purposes of the present disclosure, includes a DNA region encoding a gene product (see infra), as well as all DNA regions which regulate the production of the gene product, whether or not such regulatory sequences are adjacent to coding and/or transcribed sequences. Accordingly, a gene includes, but is not necessarily limited to, promoter sequences, terminators, translational regulatory sequences such as ribosome binding sites and internal ribosome entry sites, enhancers, silencers, insulators, boundary elements, replication origins, matrix attachment sites and locus control regions.

"Gene expression" refers to the conversion of the information, contained in a gene, into a gene product. A gene product can be the direct transcriptional product of a gene (e.g., mRNA, tRNA, rRNA, antisense RNA, ribozyme, structural RNA or any other type of RNA) or a protein produced by translation of a mRNA. Gene products also include RNAs which are modified, by processes such as capping, polyadenylation, methylation, and editing, and proteins modified by, for example, methylation, acetylation, phosphorylation, ubiquitination, ADP-ribosylation, myristilation, and glycosylation.

"Modulation" of gene expression refers to a change in the activity of a gene. Modulation of expression can include, but is not limited to, gene activation and gene repression.

"Eucaryotic" cells include, but are not limited to, fungal cells (such as yeast), plant cells, animal cells, mammalian cells and human cells.

A "region of interest" is any region of cellular chromatin, such as, for example, a gene or a non-coding sequence within or adjacent to a gene, in which it is desirable to bind an exogenous molecule. Binding can be for the purposes of targeted DNA cleavage and/or targeted recombination. A region of interest can be present in a chromosome, an episome, an organellar genome (e.g., mitochondrial, chloroplast), or an infecting viral genome, for example. A region of interest can be within the coding region of a gene, within transcribed non-coding regions such as, for example, leader sequences, trailer sequences or introns, or within non-transcribed regions, either upstream or downstream of the coding region. A region of interest can be as small as a single nucleotide pair or up to 2,000 nucleotide pairs in length, or any integral value of nucleotide pairs.

The terms "operative linkage" and "operatively linked" (or "operably linked") are used interchangeably with reference to a juxtaposition of two or more components (such as sequence elements), in which the components are arranged such that both components function normally and allow the possibility that at least one of the components can mediate a function that is exerted upon at least one of the other components. By way of illustration, a transcriptional regulatory sequence, such as a promoter, is operatively linked to a coding sequence if the transcriptional regulatory sequence controls the level of transcription of the coding sequence in response to the presence or absence of one or more transcriptional regulatory factors. A transcriptional regulatory sequence is generally operatively linked in cis with a coding sequence, but need not be directly adjacent to it. For example, an enhancer is a transcriptional regulatory sequence that is operatively linked to a coding sequence, even though they are not contiguous.

With respect to fusion polypeptides, the term "operatively linked" can refer to the fact that each of the components performs the same function in linkage to the other component as it would if it were not so linked. For example, with respect to a fusion polypeptide in which a ZFP DNA-binding domain is fused to a cleavage domain, the ZFP DNA-binding domain and the cleavage domain are in operative linkage if, in the fusion polypeptide, the ZFP DNA-binding domain portion is able to bind its target site and/or its binding site, while the cleavage domain is able to cleave DNA in the vicinity of the target site.

A "functional fragment" of a protein, polypeptide or nucleic acid is a protein, polypeptide or nucleic acid whose sequence is not identical to the full-length protein, polypeptide or nucleic acid, yet retains the same function as the full-length protein, polypeptide or nucleic acid. A functional fragment can possess more, fewer, or the same number of residues as the corresponding native molecule, and/or can contain one ore more amino acid or nucleotide substitutions. Methods for determining the function of a nucleic acid (e.g., coding function, ability to hybridize to another nucleic acid) are well-known in the art. Similarly, methods for determining protein function are well-known. For example, the DNA-binding function of a polypeptide can be determined, for example, by filter-binding, electrophoretic mobility-shift, or immunoprecipitation assays. DNA cleavage can be assayed by gel electrophoresis. See Ausubel et al., supra. The ability of a protein to interact with another protein can be determined, for example, by co-immunoprecipitation, two-hybrid assays or complementation, both genetic and biochemical. See, for example, Fields et al. (1989) *Nature* 340:245-246; U.S. Pat. No. 5,585,245 and PCT WO 98/44350.

Engineered Cleavage Half-Domains

Engineered cleavage half-domains (also referred to as dimerization domain mutants) that minimize or prevent homodimerization are described for example in U.S. Patent Publication Nos. 20050064474 and 20060188987, incorporated by reference in their entireties herein. Amino acid residues at positions 446, 447, 479, 483, 484, 486, 487, 490, 491, 496, 498, 499, 500, 531, 534, 537, and 538 of Fok I are all targets for influencing dimerization of the Fok I cleavage half-domains. Numbering of amino acid residues in the FokI protein is according to Wah et al., (1998) *Proc Natl Acad Sci USA* 95:10564-10569.

Described herein are engineered cleavage half-domains of Fok I that form an obligate heterodimer. Exemplary mutant cleavage half-domains are shown in Table 1. In certain embodiments, the cleavage half-domain includes mutations at one or both of amino acid residues at positions 490 and 538 of Fok I. In other embodiments, the second cleavage half-domain includes mutations at one or more of amino acid residues 486 and 499. See, FIGS. 1-3; Examples.

In one embodiment, and as shown in FIGS. 2 and 3, the mutation at 490 replaces Glu (E) with Lys (K); the mutation at 538 replaces Ile (I) with Lys (K); the mutation at 486 replaced Gln (Q) with Glu (E); and the mutation at position 499 replaces Ile (I) with Lys (K). Specifically, the engineered cleavage half-domains described herein were prepared by mutating positions 490 (E→K) and 538 (I→K) in one cleavage half-domain to produce an engineered cleavage half-domain designated "E490K:I538K" and by mutating positions 486 (Q→E) and 499 (I→L) in another cleavage half-domain to produce an engineered cleavage half-domain designated "Q486E:I499L". The engineered cleavage half-domains described herein are obligate heterodimer mutants in which aberrant cleavage is minimized or abolished. See Examples.

Engineered cleavage half-domains described herein can be prepared using any suitable method, for example, by site-directed mutagenesis of wild-type cleavage half-domains (Fok I) as described in Example 5 of U.S. Patent Publication No. 20050064474 and Examples 5 and 38 of International Patent Publication WO 07/014275.

Fusion Proteins

The engineered cleavage half-domains described herein are advantageously used in fusion proteins with ZFPs to specifically target sites for cleavage in any cell.

Selection of target sites; ZFPs and methods for design and construction of fusion proteins (and polynucleotides encoding same) are known to those of skill in the art and described in detail in U.S. Patent Publication Nos. 20050064474 and 20060188987, incorporated by reference in their entireties herein.

The ZFNs described herein may be delivered to a target cell by any suitable means. Methods of delivering proteins comprising zinc fingers are described, for example, in U.S. Pat. Nos. 6,453,242; 6,503,717; 6,534,261; 6,599,692; 6,607,882; 6,689,558; 6,824,978; 6,933,113; 6,979,539; 7,013,219; and 7,163,824, the disclosures of all of which are incorporated by reference herein in their entireties.

ZFNs as described herein may also be delivered using vectors containing sequences encoding one or more ZFNs. Any vector systems may be used including, but not limited to, plasmid vectors, retroviral vectors, lentiviral vectors, adenovirus vectors, poxvirus vectors; herpesvirus vectors and adeno-associated virus vectors, etc. See, also, U.S. Pat. Nos. 6,534,261; 6,607,882; 6,824,978; 6,933,113; 6,979,539; 7,013,219; and 7,163,824, incorporated by reference herein in their entireties.

Conventional viral and non-viral based gene transfer methods can be used to introduce nucleic acids encoding ZFNs comprising engineered cleavage domains in cells (e.g., mammalian cells) and target tissues. Such methods can also be used to administer such nucleic acids to cells in vitro. In certain embodiments, nucleic acids encoding ZFNs are administered for in vivo or ex vivo gene therapy uses. Non-viral vector delivery systems include DNA plasmids, naked nucleic acid, and nucleic acid complexed with a delivery vehicle such as a liposome or poloxamer. Viral vector delivery systems include DNA and RNA viruses, which have either episomal or integrated genomes after delivery to the cell. For a review of gene therapy procedures, see Anderson, *Science* 256:808-813 (1992); Nabel & Felgner, *TIBTECH* 11:211-217 (1993); Mitani & Caskey, *TIBTECH* 11:162-166 (1993); Dillon, *TIBTECH* 11:167-175 (1993); Miller, *Nature* 357: 455-460 (1992); Van Brunt, *Biotechnology* 6(10):1149-1154 (1988); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* Doerfler and Bohm (eds.) (1995); and Yu et al., *Gene Therapy* 1:13-26 (1994).

Methods of non-viral delivery of nucleic acids encoding ZFNs include electroporation, lipofection, microinjection, biolistics, virosomes, liposomes, immunoliposomes, polycation or lipid:nucleic acid conjugates, naked DNA, artificial virions, and agent-enhanced uptake of DNA. Sonoporation using, e.g., the Sonitron 2000 system (Rich-Mar) can also be used for delivery of nucleic acids.

Additional exemplary nucleic acid delivery systems include those provided by Amaxa Biosystems (Cologne, Germany), Maxcyte, Inc. (Rockville, Md.) and BTX Molecular Delivery Systems (Holliston, Mass.).

Lipofection is described in e.g., U.S. Pat. Nos. 5,049,386; 4,946,787; and 4,897,355) and lipofection reagents are sold commercially (e.g., Transfectam™ and Lipofectin™). Cationic and neutral lipids that are suitable for efficient receptor-recognition lipofection of polynucleotides include those of Felgner, WO 91/17424, WO 91/16024. Delivery can be to cells (ex vivo administration) or target tissues (in vivo administration).

The preparation of lipid:nucleic acid complexes, including targeted liposomes such as immunolipid complexes, is well known to one of skill in the art (see, e.g., Crystal, *Science* 270:404-410 (1995); Blaese et al., *Cancer Gene Ther.* 2:291-297 (1995); Behr et al., *Bioconjugate Chem.* 5:382-389 (1994); Remy et al., *Bioconjugate Chem.* 5:647-654 (1994); Gao et al., *Gene Therapy* 2:710-722 (1995); Ahmad et al., *Cancer Res.* 52:4817-4820 (1992); U.S. Pat. Nos. 4,186,183, 4,217,344, 4,235,871, 4,261,975, 4,485,054, 4,501,728, 4,774,085, 4,837,028, and 4,946,787).

The use of RNA or DNA viral based systems for the delivery of nucleic acids encoding ZFNs comprising engineered cleavage half-domains as described herein take advantage of highly evolved processes for targeting a virus to specific cells in the body and trafficking the viral payload to the nucleus. Viral vectors can be administered directly to patients (in vivo) or they can be used to treat cells in vitro and the modified cells are administered to patients (ex vivo). Conventional viral based systems for the delivery of ZFNs include, but are not limited to, retroviral, lentivirus, adenoviral, adeno-associated, vaccinia and herpes simplex virus vectors for gene transfer. Integration in the host genome is possible with the retrovirus, lentivirus, and adeno-associated virus gene transfer methods, often resulting in long term.expression of the inserted transgene. Additionally, high transduction efficiencies have been observed in many different cell types and target tissues.

The tropism of a retrovirus can be altered by incorporating foreign envelope proteins, expanding the potential target population of target cells. Lentiviral vectors are retroviral vectors that are able to transduce or infect non-dividing cells and typically produce high viral titers. Selection of a retroviral gene transfer system depends on the target tissue. Retroviral vectors are comprised of cis-acting long terminal repeats with packaging capacity for up to 6-10 kb of foreign sequence. The minimum cis-acting LTRs are sufficient for replication and packaging of the vectors, which are then used to integrate the therapeutic gene into the target cell to provide permanent transgene expression. Widely used retroviral vectors include those based upon murine leukemia virus (MuLV), gibbon ape leukemia virus (GaLV), Simian Immunodeficiency virus (SIV), human immunodeficiency virus (HIV), and combinations thereof (see, e.g., Buchscher et al., *J. Virol.* 66:2731-2739 (1992); Johann et al., *J. Virol.* 66:1635-1640 (1992); Sommerfelt et al., *Virol.* 176:58-59 (1990); Wilson et al., *J. Virol.* 63:2374-2378 (1989); Miller et al., *J. Virol.* 65:2220-2224 (1991); PCT/US94/05700).

In applications in which transient expression of a ZFP fusion protein is preferred, adenoviral based systems can be used. Adenoviral based vectors are capable of very high transduction efficiency in many cell types and do not require cell division. With such vectors, high titer and high levels of expression have been obtained. This vector can be produced in large quantities in a relatively simple system. Adeno-associated virus ("AAV") vectors are also used to transduce cells with target nucleic acids, e.g., in the in vitro production of nucleic acids and peptides, and for in vivo and ex vivo gene therapy procedures (see, e.g., West et al., *Virology* 160:38-47 (1987); U.S. Pat. No. 4,797,368; WO 93/24641; Kotin, *Human Gene Therapy* 5:793-801 (1994); Muzyczka, *J. Clin. Invest.* 94:1351 (1994). Construction of recombinant AAV vectors are described in a number of publications, including U.S. Pat. No. 5,173,414; Tratschin et al., *Mol. Cell. Biol.* 5:3251-3260 (1985); Tratschin, et al., *Mol. Cell. Biol.* 4:2072-2081 (1984); Hermnonat & Muzyczka, *PNAS* 81:6466-6470 (1984); and Samulski et al., *J. Virol.* 63:03822-3828 (1989).

At least six viral vector approaches are currently available for gene transfer in clinical trials, which utilize approaches that involve complementation of defective vectors by genes inserted into helper cell lines to generate the transducing agent.

pLASN and MFG-S are examples of retroviral vectors that have been used in clinical trials (Dunbar et al., *Blood* 85:3048-305 (1995); Kohn et al., *Nat. Med.* 1:1017-102 (1995); Malech et al., *PNAS* 94:22 12133-12138-(1997)). PA317/pLASN was the first therapeutic vector used in a gene therapy trial. (Blaese et al., *Science* 270:475-480 (1995)). Transduction efficiencies of 50% or greater have been observed for MFG-S packaged vectors. (Ellem et al., *Immunol Immunother.* 44(1):10-20 (1997); Dranoff et al., *Hum. Gene Ther.* 1:111-2 (1997).

Recombinant adeno-associated virus vectors (rAAV) are a-promising alternative gene delivery systems based on the defective and nonpathogenic parvovirus adeno-associated type 2 virus. All vectors are derived from a plasmid that retains only the AAV 145 bp inverted terminal repeats flanking the transgene expression cassette. Efficient gene transfer and stable transgene delivery due to integration into the genomes of the transduced cell are key features for this vector system. (Wagner et al., *Lancet* 351:9117 1702-3 (1998), Kearns et al., *Gene Ther.* 9:748-55 (1996)).

Replication-deficient recombinant adenoviral vectors (Ad) can be produced at high titer and readily infect a number of different cell types. Most adenovirus vectors are engineered such that a transgene replaces the Ad E1a, E1b, and/or E3 genes; subsequently the replication defective vector is propagated in human 293 cells that supply deleted gene function in trans. Ad vectors can transduce multiple types of tissues in vivo, including nondividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., *Hum. Gene Ther.* 7:1083-9 (1998)). Additional examples of the use of adenovirus vectors for gene transfer in clinical trials include Rosenecker et al., *Infection* 24:1 5-10 (1996); Sterman et al., *Hum. Gene Ther.* 9:7 1083-1089 (1998); Welsh et al., *Hum. Gene Ther.* 2:205-18 (1995); Alvarez et al., *Hum. Gene Ther.* 5:597-613 (1997); Topf et al., *Gene Ther.* 5:507-513 (1998); Sterman et al., *Hum. Gene Ther.* 7:1083-1089 (1998).

In certain embodiments, the vector is an adenovirus vector. Thus, described herein are adenovirus (Ad) vectors for introducing heterologous sequences (e.g., zinc finger nucleases (ZFNs)) into cells.

Non-limiting examples of Ad vectors that can be used in the present application include recombinant (such as E1-deleted), conditionally replication competent (such as oncolytic) and/or replication competent Ad vectors derived from human or non-human serotypes (e.g., Ad5, Ad11, Ad35, or porcine adenovirus-3); and/or chimeric Ad vectors (such as Ad5/35) or tropism-altered Ad vectors with engineered fiber (e.g., knob or shaft) proteins (such as peptide insertions within the HI loop of the knob protein). Also useful are "gutless" Ad vectors, e.g., an Ad vector in which all adenovirus genes have been removed, to reduce immunogenicity and to increase the size of the DNA payload. This allows, for example, simultaneous delivery of sequences encoding ZFNs and a donor sequence. Such gutless vectors are especially useful when the donor sequences include large transgenes to be integrated via targeted integration.

Replication-deficient recombinant adenoviral vectors (Ad) can be produced at high titer, and they readily infect a number of different cell types. Most adenovirus vectors are engineered such that a transgene replaces the Ad E1a, E1b, and/or E3 genes; subsequently the replication defective vector is propagated in cells that provide one or more of the deleted gene functions in trans. For example, human 293 cells supply E1 function. Ad vectors can transduce multiple types of tissues in vivo, including non-dividing, differentiated cells such as those found in liver, kidney and muscle. Conventional Ad vectors have a large carrying capacity. An example of the use of an Ad vector in a clinical trial involved polynucleotide therapy for antitumor immunization with intramuscular injection (Sterman et al., Hum. Gene Ther. 7:1083-1089 (1998)).

Additional examples of the use of adenovirus vectors for gene transfer in clinical trials include Rosenecker et al., Infection 24:1 5-10 (1996); Welsh et al., Hum. Gene Ther. 2:205-18 (1995); Alvarez et al., Hum. Gene Ther. 5:597-613 (1997); Topf et al., Gene Ther. 5:507-513 (1998).

In certain embodiments, the Ad vector is a chimeric adenovirus vector, containing sequences from two or more different adenovirus genomes. For example, the Ad vector can be an Ad5/35 vector. Ad5/35 is created by replacing one or more of the fiber protein genes (knob, shaft, tail, penton) of Ad5 with the corresponding fiber protein gene from a B group adenovirus such as, for example, Ad35. The Ads/35 vector and characteristics of this vector are described, for example, in Ni et al. (2005) "Evaluation of biodistribution and safety of adenovirus vectors containing group B fibers after intravenous injection into baboons," Hum Gene Ther 16:664-677; Nilsson et al. (2004) "Functionally distinct subpopulations of cord blood CD34+ cells are transduced by adenoviral vectors with serotype 5 or 35 tropism," Mol Ther 9:377-388; Nilsson et al. (2004) "Development of an adenoviral vector system with adenovirus serotype 35 tropism; efficient transient gene transfer into primary malignant hematopoietic cells," J Gene Med 6:631-641; Schroers et al. (2004) "Gene transfer into human T lymphocytes and natural killer cells by Ad5/F35 chimeric adenoviral vectors," Exp Hematol 32:536-546; Seshidhar et al. (2003) "Development of adenovirus serotype 35 as a gene transfer vector," Virology 311:384-393; Shayakhmetov et al. (2000) "Efficient gene transfer into human CD34(+) cells by a retargeted adenovirus vector," J Virol 74:2567-2583; and Sova et al. (2004), "A tumor-targeted and conditionally replicating oncolytic adenovirus vector expressing TRAIL for treatment of liver metastases," Mol Ther 9:496-509.

Packaging cells are used to form virus particles that are capable of infecting a host cell. Such cells include 293 cells, which package adenovirus, and ψ2 cells or PA317 cells, which package retrovirus. Viral vectors used in gene therapy are usually generated by a producer cell line that packages a nucleic acid vector into a viral particle. The vectors typically contain the minimal viral sequences required for packaging and subsequent integration into a host (if applicable), other viral sequences being replaced by an expression cassette encoding the protein to be expressed. The missing viral functions are supplied in trans by the packaging cell line. For example, AAV vectors used in gene therapy typically only possess inverted terminal repeat (ITR) sequences from the AAV genome which are required for packaging and integration into the host genome. Viral DNA is packaged in a cell line, which contains a helper plasmid encoding the other AAV genes, namely rep and cap, but lacking ITR sequences. The cell line is also infected with adenovirus as a helper. The helper virus promotes replication of the AAV vector and expression of AAV genes from the helper plasmid. The helper plasmid is not packaged in significant amounts due to a lack of ITR sequences. Contamination with adenovirus can be reduced by, e.g., heat treatment to which adenovirus is more sensitive than AAV.

In many gene therapy applications, it is desirable that the gene therapy vector be delivered with a high degree of specificity to a particular tissue type. Accordingly, a viral vector can be modified to have specificity for a given cell type by expressing a ligand as a fusion protein with a viral coat protein on the outer surface of the virus. The ligand is chosen to have affinity for a receptor known to be present on the cell type of interest. For example, Han et al., *Proc. Natl. Acad. Sci. USA* 92:9747-9751 (1995), reported that Moloney murine leukemia virus can be modified to express human heregulin fused to gp70, and the recombinant virus infects certain human breast cancer cells expressing human epidermal growth factor receptor. This principle can be extended to other virus-target cell pairs, in which the target cell expresses a receptor and the virus expresses a fusion protein comprising a ligand for the cell-surface receptor. For example, filamentous phage can be engineered to display antibody fragments (e.g., FAB or Fv) having specific binding affinity for virtually any chosen cellular receptor. Although the above description applies primarily to viral vectors, the same principles can be applied to nonviral vectors. Such vectors can be engineered to contain specific uptake sequences which favor uptake by specific target cells.

Gene therapy vectors can be delivered in vivo by administration to an individual patient, typically by systemic administration (e.g., intravenous, intraperitoneal, intramuscular, subdermal, or intracranial infusion) or topical application, as described below. Alternatively, vectors can be delivered to cells ex vivo, such as cells explanted from an individual patient (e.g., lymphocytes, bone marrow aspirates, tissue biopsy) or universal donor hematopoietic stem cells, followed by reimplantation of the cells into a patient, usually after selection for cells which have incorporated the vector.

Ex vivo cell transfection for diagnostics, research, or for gene therapy (e.g., via re-infusion of the transfected cells into the host organism) is well known to those of skill in the art. In a preferred embodiment, cells are isolated from the subject organism, transfected with a ZFN nucleic acid (gene or cDNA), and re-infused back into the subject organism (e.g., patient). Various cell types suitable for ex vivo transfection are well known to those of skill in the art (see, e.g., Freshney et al., *Culture of Animal Cells, A Manual of Basic Technique* (3rd ed. 1994)) and the references cited therein for a discussion of how to isolate and culture cells from patients).

In one embodiment, stem cells are used in ex vivo procedures for cell transfection and gene therapy. The advantage to using stem cells is that they can be differentiated into other cell types in vitro, or can be introduced into a mammal (such as the donor of the cells) where they will engraft in the bone marrow. Methods for differentiating CD34+ cells in vitro into clinically important immune cell types using cytokines such a GM-CSF, IFN-γ and TNF-α are known (see Inaba et al., *J. Exp. Med.* 176:1693-1702 (1992)).

Stem cells are isolated for transduction and differentiation using known methods. For example, stem cells are isolated from bone marrow cells by panning the bone marrow cells with antibodies which bind unwanted cells, such as CD4+ and CD8+ (T cells), CD45+ (panB cells), GR-1 (granulocytes), and lad (differentiated antigen presenting cells) (see Inaba et al., *J. Exp. Med.* 176:1693-1702 (1992)).

Vectors (e.g., retroviruses, adenoviruses, liposomes, etc.) containing therapeutic ZFP nucleic acids can also be administered directly to an organism for transduction of cells in vivo. Alternatively, naked DNA can be administered. Administration is by any of the routes normally used for introducing a molecule into ultimate contact with blood or tissue cells including, but not limited to, injection, infusion, topical application and electroporation. Suitable methods of administering such nucleic acids are available and well known to those of skill in the art, and, although more than one route can be used to administer a particular composition, a particular route can often provide a more immediate and more effective reaction than another route.

Methods for introduction of DNA into hematopoietic stem cells are disclosed, for example, in U.S. Pat. No. 5,928,638. Vectors useful for introduction of transgenes into hematopoietic stem cells, e.g., CD34+ cells, include adenovirus Type 35.

Vectors suitable for introduction of transgenes into immune cells (e.g., T-cells) include non-integrating lentivirus vectors. See, for example, Ory et al. (1996) *Proc. Natl. Acad. Sci. USA* 93:11382-11388; Dull et al. (1998) *J. Virol.* 72:8463-8471; Zuffery et al. (1998) *J. Virol.* 72:9873-9880; Follenzi et al. (2000) *Nature Genetics* 25:217-222.

Pharmaceutically acceptable carriers are determined in part by the particular composition being administered, as well as by the particular method used to administer the composition. Accordingly, there is a wide variety of suitable formulations of pharmaceutical compositions available, as described below (see, e.g., *Remington's Pharmaceutical Sciences,* 17th ed., 1989).

As noted above, the disclosed methods and compositions can be used in any type of cell including, but not limited to, prokaryotic cells, fungal cells, Archaeal cells, plant cells, insect cells, animal cells, vertebrate cells, mammalian cells and human cells. Suitable cell lines for protein expression are known to those of skill in the art and include, but are not limited to COS, CHO (e.g., CHO-S, CHO-K1, CHO-DG44, CHO-DUXB11), VERO, MDCK, WI38, V79, B14AF28-G3, BHK, HaK, NSO, SP2/0-Ag14, HeLa, HEK293 (e.g., HEK293-F, HEK293-H, HEK293-T), perC6, insect cells such as *Spodoptera fugiperda* (Sf), and fungal cells such as *Saccharomyces, Pischia* and *Schizosaccharomyces.* Progeny, variants and derivatives of these cell lines can also be used.

Applications

The disclosed cleavage domains are advantageously used in combination with zinc finger proteins to cleave DNA and minimize off-target site cleavage (as compared to ZFNs comprising wild-type or homodimerizing cleavage domains). Cleavage can be at a region of interest in cellular chromatin. (e.g., at a desired or predetermined site in a genome, for example, in a gene, either mutant or wild-type); to replace a genomic sequence (e.g., a region of interest in cellular chromatin) with a homologous non-identical sequence (i.e., targeted recombination); to delete a genomic sequence by cleaving DNA at one or more sites in the genome, which cleavage sites are then joined by non-homologous end joining (NHEJ); to screen for cellular factors that facilitate homologous recombination; and/or to replace a wild-type sequence with a mutant sequence, or to convert one allele to a different allele. Such methods are described in detail, for example, in U.S. Patent Publication No. 20050064474; International Patent Publication WO 07/014275, incorporated by reference in their entireties herein.

Accordingly, the disclosed engineered cleavage half domains can be used in any ZFN for any method in which specifically targeted cleavage is desirable and/or to replace any genomic sequence with a homologous, non-identical sequence. For example, a mutant genomic sequence can be replaced by its wild-type counterpart, thereby providing methods for treatment of e.g., genetic disease, inherited disorders, cancer, and autoimmune disease. In like fashion, one allele of a gene can be replaced by a different allele using the methods of targeted recombination disclosed herein. Indeed, any pathology dependent upon a particular genomic sequence, in any fashion, can be corrected or alleviated using the methods and compositions disclosed herein.

Exemplary genetic diseases include, but are not limited to, achondroplasia, achromatopsia, acid maltase deficiency, adenosine deaminase deficiency (OMIM No. 102700), adrenoleukodystrophy, aicardi syndrome, alpha-1 antitrypsin deficiency, alpha-thalassemia, androgen insensitivity syndrome, apert syndrome, arrhythmogenic right ventricular, dysplasia, ataxia telangictasia, barth syndrome, beta-thalassemia, blue rubber bleb nevus syndrome, canavan disease, chronic granulomatous diseases (CGD), cri du chat syndrome, cystic fibrosis, dercum's disease, ectodermal dysplasia, fanconi anemia, fibrodysplasia ossificans progressive, fragile X syndrome, galactosemis, Gaucher's disease, generalized gangliosidoses (e.g., GM1), hemochromatosis, the hemoglobin C mutation in the $6^{th}$ codon of beta-globin (HbC), hemophilia, Huntington's disease, Hurler Syndrome, hypophosphatasia, Klinefleter syndrome, Krabbes Disease, Langer-Giedion Syndrome, leukocyte adhesion deficiency (LAD, OMIM No. 116920), leukodystrophy, long QT syndrome, Marfan syndrome, Moebius syndrome, mucopolysaccharidosis (MPS), nail patella syndrome, nephrogenic diabetes insipidius, neurofibromatosis, Neimann-Pick disease, osteogenesis imperfecta, porphyria, Prader-Willi syndrome, progeria, Proteus syndrome, retinoblastoma, Rett syndrome, Rubinstein-Taybi syndrome, Sanfilippo syndrome, severe combined immunodeficiency (SCID), Shwachman syndrome, sickle cell disease (sickle cell anemia), Smith-Magenis syndrome, Stickler syndrome, Tay-Sachs disease, Thrombocytopenia Absent Radius (TAR) syndrome, Treacher Collins syndrome, trisomy, tuberous sclerosis, Turner's syndrome, urea cycle disorder, von Hippel-Landau disease, Waardenburg syndrome, Williams syndrome, Wilson's disease, Wiskott-Aldrich syndrome, X-linked lymphoproliferative syndrome (XLP, OMIM No. 308240).

Additional exemplary diseases that can be treated by targeted DNA cleavage and/or homologous recombination include acquired immunodeficiencies, lysosomal storage diseases (e.g., Gaucher's disease, GM1, Fabry disease and Tay-Sachs disease), mucopolysaccahidosis (e.g. Hunter's disease, Hurler's disease), hemoglobinopathies (e.g., sickle cell diseases, HbC, α-thalassemia, β-thalassemia) and hemophilias.

Such methods also allow for treatment of infections (viral or bacterial) in a host (e.g., by blocking expression of viral or bacterial receptors, thereby preventing infection and/or spread in a host organism); to treat genetic diseases.

Targeted cleavage of infecting or integrated viral genomes can be used to treat viral infections in a host. Additionally, targeted cleavage of genes encoding receptors for viruses can be used to block expression of such receptors, thereby preventing viral infection and/or viral spread in a host organism. Targeted mutagenesis of genes encoding viral receptors (e.g., the CCR5 and CXCR4 receptors for HIV) can be used to render the receptors unable to bind to virus, thereby preventing new infection and blocking the spread of existing infections. See, U.S. Patent Publication No. 20080159996. Non-limiting examples of viruses or viral receptors that may be targeted include herpes simplex virus (HSV), such as HSV-1 and HSV-2, varicella zoster virus (VZV), Epstein-Barr virus (EBV) and cytomegalovirus (CMV), HHV6 and HHV7. The hepatitis family of viruses includes hepatitis A virus (HAV), hepatitis B virus (HBV), hepatitis C virus (HCV), the delta hepatitis virus (HDV), hepatitis E virus (HEV) and hepatitis G virus (HGV). Other viruses or their receptors may be targeted, including, but not limited to, Picornaviridae (e.g., polioviruses, etc.), Caliciviridae; Togaviridae (e.g., rubella virus, dengue virus, etc.); Flaviviridae; Coronaviridae; Reoviridae; Birnaviridae; Rhabodoviridae (e.g., rabies virus, etc.); Filoviridae; Paramyxoviridae (e.g., mumps virus, measles virus, respiratory syncytial virus, etc.); Orthomyxoviridae (e.g., influenza virus types A, B and C, etc.); Bunyaviridae; Arenaviridae; Retroviradae; lentiviruses (e.g., HTLV-I; HTLV-II; HIV-1 (also known as HTLV-III, LAV, ARV, hTLR, etc.) HIV-II); simian immunodeficiency virus (SIV), human papillomavirus (HPV), influenza virus and the tick-borne encephalitis viruses. See, e.g. Virology, 3rd Edition (W. K. Joklik ed. 1988); Fundamental Virology, 2nd Edition (B. N. Fields and D. M. Knipe, eds. 1991), for a description of these and other viruses. Receptors for HIV, for example, include CCR-5 and CXCR-4.

Thus, heterodimeric cleavage domain variants as described herein provide broad utility for improving ZFN specificity in gene modification applications. These variant cleavage domains may be readily incorporated into any existing ZFN by either site directed mutagenesis or subdloning to improve the in vivo specificity of any ZFN dimers.

As noted above, the compositions and methods described herein can be used for gene modification, gene correction, and gene disruption. Non-limiting examples of gene modification includes homology directed repair (HDR)-based targeted integration; HDR-based gene correction; HDR-based gene modification; HDR-based gene disruption; NHEJ-based gene disruption and/or combinations of HDR, NHEJ, and/or single strand annealing (SSA). Single-Strand Annealing (SSA) refers to the repair of a double strand break between two repeated sequences that occur in the same orientation by resection of the DSB by 5'-3' exonucleases to expose the 2 complementary regions. The single-strands encoding the 2 direct repeats then anneal to each other, and the annealed intermediate can be processed such that the single-stranded tails (the portion of the single-stranded DNA that is not annealed to any sequence) are be digested away, the gaps filled in by DNA Polymerase, and the DNA ends rejoined. This results in the deletion of sequences located between the direct repeats.

Compositions comprising cleavage domains (e.g., ZFNs) and methods described herein can also be used in the treatment of various genetic diseases and/or infectious diseases.

The compositions and methods can also be applied to stem cell based therapies, including but not limited to:

(a) Correction of somatic cell mutations by short patch gene conversion or targeted integration for monogenic gene therapy (b) Disruption of dominant negative alleles (c) Disruption of genes required for the entry or productive infection of pathogens into cells (d) Enhanced tissue engineering, for example, by:
  (i) Modifying gene activity to promote the differentiation or formation of functional tissues; and/or
  (ii) Disrupting gene activity to promote the differentiation or formation of functional tissues (e) Blocking or inducing differentiation, for example, by:
  (i) Disrupting genes that block differentiation to promote stem cells to differentiate down a specific lineage pathway (ii) Targeted insertion of a gene or siRNA expression cassette that can stimulate stem cell differentiation.
  (iii) Targeted insertion of a gene or siRNA expression cassette that can block stem cell differentiation and allow better expansion and maintenance of pluripotency
  (iv) Targeted insertion of a reporter gene in frame with an endogenous gene that is a marker of pluripotency or differentiation state that would allow an easy marker to score differentiation state of stem cells and how changes in media, cytokines, growth conditions, expression of genes, expression of siRNA molecules, exposure to antibodies to cell surface markers, or drugs alter this state.

(f) Somatic cell nuclear transfer, for example, a patient's own somatic cells can be isolated, the intended target gene modified in the appropriate manner, cell clones generated (and quality controlled to ensure genome safety), and the nuclei from these cells isolated and transferred into unfertilized eggs to generate patient-specific hES cells that could be directly injected or differentiated before engrafting into the patient, thereby reducing or eliminating tissue rejection.

(g) Universal stem cells by knocking out MHC receptors—This approach would be used to generate cells of diminished or altogether abolished immunological identity. Cell types for this procedure include but are not limited to, T-cells, B cells, hematopoietic stem cells, and embryonic stem cells. Therefore, these stem cells or their derivatives (differentiated cell types or tissues) could be potentially engrafted into any person regardless of their origin or histocompatibility.

The compositions and methods can also be used for somatic cell therapy (e.g., autologus cell therapy and/or universal T-cell by knocking out MHC receptors, see section (g) above), thereby allowing production of stocks of T-cells that have been modified to enhance their biological properties. Such cells can be infused into a variety of patients independent of the donor source of the T-cells and their histocompatibility to the recipient.

In addition to therapeutic applications, the increased specificity provided by the variants described herein when used in ZFNs can be used for crop engineering, cell line engineering and the construction of disease models. The obligate heterodimer cleavage half-domains provide a straightforward means for improving ZFN properties, especially when homodimer activity limits efficacy.

The engineered cleavage half domains described can also be used in gene modification protocols requiring simultaneous cleavage at multiple targets either to delete the intervening region or to alter two specific loci at once. Cleavage at two targets would require cellular expression of four ZFNs, which would yield ten different active ZFN combinations. For such applications, substitution of our variants for the wild-type nuclease domain would eliminate the activity of six of these combinations and reduce chances of off-target cleavage.

All patents, patent applications and publications mentioned herein are hereby incorporated by reference in their entireties.

Although disclosure has been provided in some detail by way of illustration and example for the purposes of clarity and understanding, it will be apparent to those of skill in the art that various changes and modifications can be practiced without departing from the spirit or scope of the disclosure. Accordingly, the foregoing disclosure and following examples should not be construed as limiting.

EXAMPLES

Example 1

Design of Engineered FokI Cleavage Half Domains

A variety of strategies have been described for constructing heterodimeric protein interaction surfaces. See, O'Shea, E. K et al. (1993) *Curr Biol* 3:658-667; Zhu et al. (1997) *Protein Sci* 6:781-788; Atwell et al. (1997) *J Mol Biol* 270:26-35; Nohaile et al. (2001) *Proc Natl Acad Sci USA* 98:3109-3114; Havranek & Harbury (2003) *Nat Struct Biol* 10:45-52; Bolon et al. (2005) *Proc Natl Acad Sci USA* 102:12724-12729. However, the development of FokI heterodimers presented challenges that required a distinct approach. One critical difference from prior strategies was that the target for redesign efforts, the FokI cleavage domain, is an enzyme. It was therefore important to screen variant designs for catalytic function instead of just interaction preference. This was a significant concern since active site residues are within 10 angstroms of the interface. See, Wah et al. (1998) *Proc Natl Acad Sci USA* 95:10564-10569.

A second feature for designing heterodimizering cleavage half-domains was the very low affinity of FokI dimerization. Our interest in preserving this property, which is important for ensuring cleavage specificity, argued against using affinity-based selection methods such as phage display for heterodimer development. A final consideration was the predominantly hydrophilic nature of the FokI dimer interface, which contains numerous electrostatic interactions as well as many ordered waters (Wah et al, supra). This feature made it less likely that a purely computational strategy would yield monomers with the desired properties.

Molecular modeling was conducted as follows. The 2FOK.pdb crystal structure served as the basis for all molecular modeling. The dimer interface was visualized using VMD version 1.8.2 run on a Silicon Graphics Octane workstation equipped with CrystalEyes3 3D visualization eyewear (stereographics). Amino acid substitutions were modeled using Swiss-Pdb Viewer version 3.7 run on a Silicon Graphics Octane workstation and using the following hydrogen bonding thresholds: a minimum distance of 2.195 Å, a maximum distance of 3.300 Å, and a minimum angle between the acceptor, donor and the atom covalently bonded to the donor of 90°. The hydrogen bonding potential of various amino acid substitutions were investigated by using the "mutate" command and then manually manipulating the torsion angles of the side chain in question with the "torsions" command. The realtime display of hydrogen bonds and steric clashes was enabled during the manual torsion manipulation. If torsion angles for a given amino acid substitution could be found that simultaneously fell within the hydrogen bonding thresholds and avoided any steric clashes, then that substitution was considered to have the potential to make a hydrogen bond in our nucleases. If interfaces with multiple amino acid substitutions were being modeled, this manual torsion manipulation alternated between the sidechains of interest until a suitable geometry for a new hydrogen bond was found or it was clear that such a new hydrogen bond was impossible. Automated energy minimization or binding energy calculations during the molecular modeling as commercially available molecular modeling software was not employed as it tends to inaccurately model hydrophilic protein interfaces.

Furthermore, a stepwise (iterative) approach was employed to produce variants as described herein by modifying the dimer interface. In particular, four cycles of variant design and testing of variants in the context of zinc finger nucleases (see, Example 2) were conducted, each of which substituted one amino acid at the dimer interface were conducted and yielded a progressively more heterodimeric ZFN complex. In each cycle, a small panel of single amino acid substitutions was generated within one cleavage domain, while its partner was not modified. The choice of substitutions was guided by the coordinates of the native FokI dimer (Wah et al. (1998) *Proc Natl Acad Sci USA* 95:10564-10569). See, FIG. 5C. Mutations were made at positions that could contact the unmodified partner, with a bias towards the introduction of charge-charge interactions. Each variant was then screened for the ability to stimulate gene correction in two alternative configurations: (i) as a heterodimer with the unmodified partner ZFN, and (ii) as a homodimer. Successive cycles alternated between the two sides of the dimer interface.

In each cycle of development, we identified a variant that efficiently induced gene correction as a heterodimer with the constant partner ZFN but that exhibited reduced activity as a homodimer. An overview of the process, along with the properties of the best-performing variant identified in each cycle, is provided in FIG. 5D.

The iterative design and screening of interface variants for progressively more heterodimeric behavior strategy described herein is also generally applicable for converting any nuclease into an obligate heterodimers.

Example 2

Construction and Testing of ZFNs with Engineered Cleavage Half-Domains

To ensure that cleavage half-domain variants retained the desired activity, the variants were incorporated into zinc finger nucleases (ZFNs) and assays using functional screens that directly tested design candidates for the ability to cleave DNA and thus induce gene correction in mammalian cells when incorporated into zinc finger nucleases were performed.

Fusion proteins comprising zinc finger proteins and modified cleavage half-domains as described herein were prepared essentially as described in U.S. Patent Publication No. 20050064474 and International Patent Publication WO2005/014791. Specifically, the amino acid sequences of the $L^{wt}$ and $R^{wt}$ ZFNs are identical to those described as ZFP-L* and ZFP-R* in Urnov (2005), supra. Mutations indicated in FIG. 5D were introduced into the region encoding the FokI cleavage domain of each ZFN using the QuikChange mutagenesis kit (Invitrogen). The $L^{wt}$ and $R^{wt}$ constructs contain residues 384 to 579 of the FokI endonuclease as described in Wah et al. (1998), supra. Several other groups use a variant of FokI that contains threonine rather than proline at position 501; this allele may be incompatible with the mutations in our cleavage domain variants.

ZFNs were assayed for functional cleavage of DNA in vitro DNA cleavage assay (Example 5) and the GFP gene correction assay described in Urnov et al. (2005) *Nature* 435:646-651 (see, also, Example 3). The GFP correction system utilizes an HEK293 cell line containing an integrated, constitutively expressed eGFP gene that is disrupted via insertion of the target for a well-characterized ZFN dimer. See, Urnov, supra; FIG. 5A; Example 3. The eGFP gene may be restored by target cleavage followed by gene correction using an eGFP donor template. The relative ability of ZFN variants to stimulate this process may be quantified by counting the fraction of cells that convert to. green fluorescence, as described in Porteus et al. (2003) *Science* 300:763. See, FIG. 5B.

The ZFN target sequence in our GFP reporter system is the binding site for the dimer ZFN-L*/ZFN-R*, which was designed for gene correction of the endogenous human IL2Rγ locus (see, Urnov et al. (2005), supra). For the sake of clarity, we will refer to the DNA binding domains of these ZFNs as the "L" and "R" ZFPs.

Results of the iterative design in terms of activity data for various constructs tested during our iterative optimization process are shown in Table 1. The earlier screening steps were performed with an in vitro DNA cleavage assay (Example 5) and the later. steps were performed using the cell-based GFP reporter gene correction assay (Example 3). Table 1 is a compilation of four separate in vitro cleavage experiments and six separate cell-based gene correction assays. All values in the "relative activity" columns were normalized to the activity of the wild-type ZFNs in that particular experiment; the absolute activity used for normalization is given in the rightmost column in terms of percent DNA cleavage (in vitro cleavage assays) or percentage of cells that score as GFP positive (for GFP gene correction experiments). The a:b heterodimer value is the relative activity of a ZFN pair containing the cleavage domain variants indicated in the "a" and "b" columns. For experiments where the "a" and "b" domains were tested in both possible orientations (i.e. L-a+R-b and R-a+L-b) the reported value is the average of these two experiments. The b:b homodimer value is the relative activity of a ZFN pair where each ZFN contains the cleavage domain variant indicated in the "b" column (a blank space indicates that particular homodimer experiment was not performed). The overall intent of the screen is to find domains that give high relative activities as heterodimers and significantly lower activity as homodirmers. A superscript 1 indicates the two constructs that performed the best in the first round of optimization and that were subsequently used as the constant partner in the second round of optimization. A superscript 2, or 3 indicates the construct that performed the best in the second or third round of optimization respectively and that was used as the constant partner in the n+1 round of optimization. The construct with the superscript 4 was the best construct in the fourth round of optimization and, along with the best construct from round 3, was determined to be our final pair of cleavage domain variants.

TABLE 1

| Optimization Round | assay type | ZFN a | ZFN b | relative activity a:b heterodimer | relative activity b:b homodimer | absolute activity of wt:wt control |
|---|---|---|---|---|---|---|
| | in vitro cleavage | R487D | D483R | 0.20 | | 54% |
| | " | " | D483K | 0.00 | | 54% |
| | " | " | Q486R | 0.00 | | 67% |
| | " | " | Q486K | 0.00 | | 67% |
| | " | R487E | D483R | 0.28 | | 54% |
| | " | " | D483K | 0.00 | | 54% |
| | " | " | Q486R | 0.00 | | 67% |
| | " | " | Q486K | 0.00 | | 67% |
| 1 | " | wt | D483L | 0.00 | | 95% |
| | " | " | Q486E | 0.00 | | 54% |
| | " | " | E490K | 1.05 | | 95% |
| | " | " | E490R$^1$ | 0.99 | 0.37 | 92% |
| | " | " | E490K$^1$ | 0.97 | 0.68 | 92% |
| | " | " | E490H | 0.96 | 0.95 | 92% |
| 2 | " | E490R$^1$ | E490D | 0.48 | 0.39 | 92% |
| | " | " | Q486E:E490D | 0.16 | 0.04 | 92% |
| | " | " | Q486D:E490D | 0.00 | 0.00 | 92% |
| | " | " | Q486E | 0.48 | 0.30 | 92% |
| | " | E490K$^1$ | E490D | 0.58 | 0.39 | 92% |
| | " | " | Q486E:E490D | 0.24 | 0.04 | 92% |
| | " | " | Q486D:E490D | 0.00 | 0.00 | 92% |
| | " | " | Q486E | 0.62 | 0.30 | 92% |
| | GFP gene correction | " | Q486E$^2$ | 0.72 | 0.19 | 0.93% |
| | " | " | Q486K | 1.03 | 0.85 | 0.62% |
| | " | " | Q486M | 1.31 | 1.32 | 0.62% |
| | " | " | Q486W | 1.40 | 1.03 | 0.62% |
| | " | " | Q486L | 0.97 | 1.28 | 0.87% |
| 3 | " | Q486E$^2$ | E490K:Q486I | 0.65 | 0.08 | 1.05% |
| | " | " | E490K:Q486L | 0.39 | 0.01 | 1.05% |
| | " | " | E490K:Q486E | 1.45 | 1.09 | 2.74% |
| | " | " | E490K:I538K$^3$ | 0.78 | 0.01 | 0.93% |
| | " | " | E490K:I538K:Q486E | 0.70 | 0.01 | 0.93% |
| | " | " | E490K:I538K:Q486I | 0.42 | 0.00 | 0.93% |
| 4 | " | E490K:I538K$^3$ | Q486E | 1.45 | 0.18 | 1.03% |
| | " | " | Q486D | 0.22 | 0.03 | 1.03% |
| | " | " | Q486E:E490D | 0.63 | 0.02 | 1.03% |
| | " | " | Q486E:I538D | 0.05 | 0.00 | 1.03% |
| | " | " | Q486E:I538E | 0.04 | 0.00 | 1.03% |
| | " | " | Q486E:I499L$^4$ | 1.67 | 0.02 | 1.03% |

In particular as shown in Table 1, our initial design efforts involved reversing the polarity of the bidendate hydrogen bond between D483 of one ZFN and R487 of its partner.

For this approach, residue D483 of one ZFN ("ZFNa") was converted to arginine or lysine, while residue R487 on the other ZFN ("ZFNb") was converted to aspartate or glutamate (Table 1, first 8 entries). In vitro cleavage analyses of these variants revealed significant (>70%) reductions in cleavage efficiency for all pairings relative to a ZFN pair containing two copies of the wild-type Fok I nuclease domain so these designs were not developed further.

Figure 5:
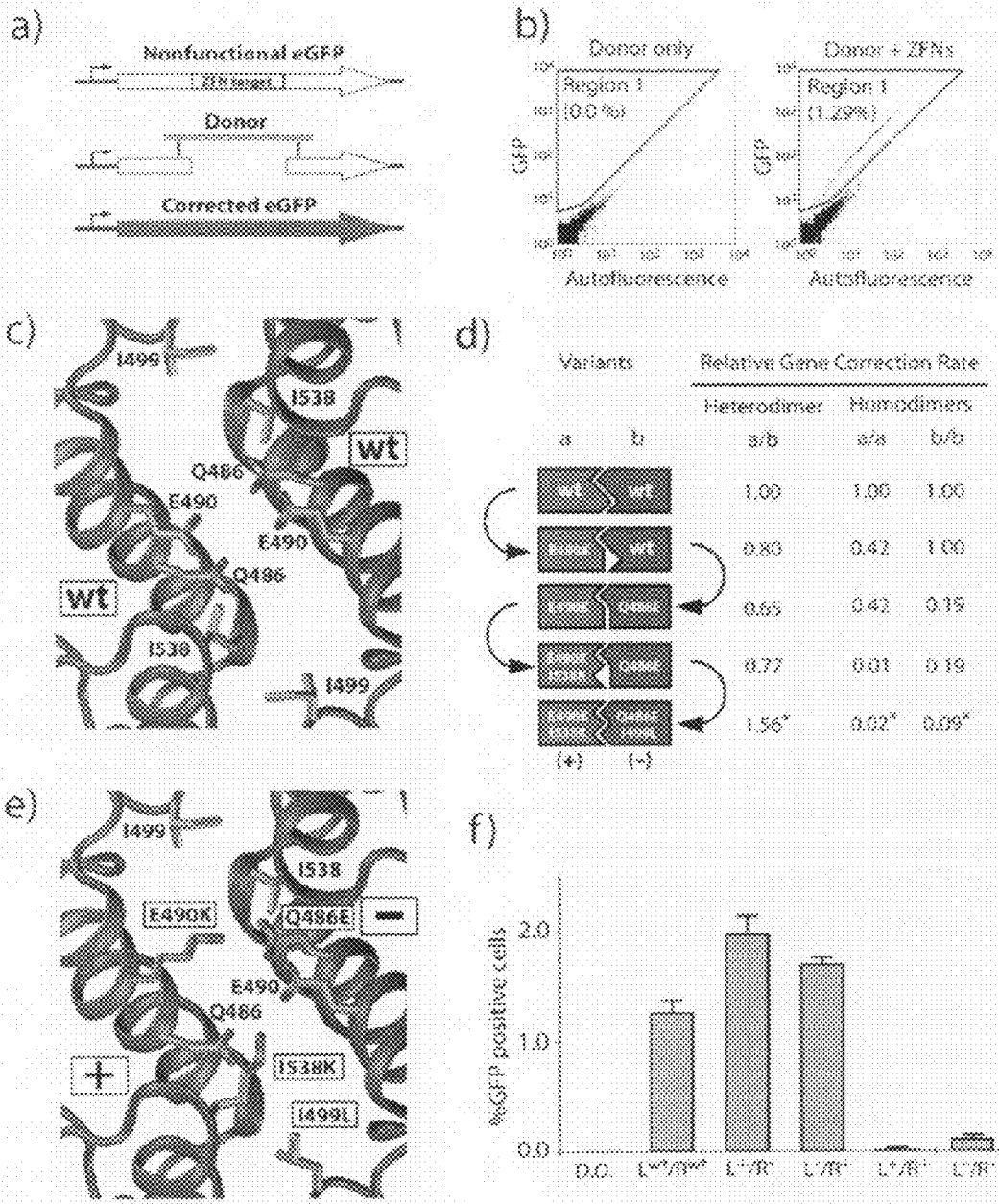
FIG. 5, panels A to F, depict exemplary zinc finger nucleases comprising engineered cleavage half-domains that function as obligate heterodimers.

After this initial attempt, we altered our development strategy to the sequential modification approach outlined in FIG. 5. For the first step of this process, we searched for a cleavage domain variant that would retain activity when paired with a copy of the wild-type domain (as a heterodimer), but would show a decrease in activity when paired with a second copy of itself (as a homodimer.)

Five single-residue substitutions were tested (Table 1, development cycle 1). The sterically conservative D483L mutant was intended to preferentially destabilize the homodimer by eliminating both of the D483-R487 interactions at the homodimer interface but only one such interaction when paired with the wild-type domain. The Q486E mutant was intended to preferentially destabilize the homodimer by adding a negatively charged residue to each side of the interface. The E490K mutant was intended to stabilize the heterodimer by potentially making a hydrogen bond to E490 of the wild-type domain and destabilize the homodimer by adding two positively charged residues to the interface and/or creating a steric clash. When paired with the wild-type domain, the E490K mutant retained full activity, but the other two mutations gave no detectable activity and were not pursued further (Table 1).

Given this result, E490R and E490H were also generated and compared with E490K for function as heterodimers with the wild type domain as well as for decreased activity as homodimers. While all variants yielded high levels of cleavage as heterodimers, only E490K and E490R lowered homodimer activity (Table 1, development cycle 1), so these two variants were advanced to the next cycle of development. The E490K mutant gave 80% of parental FokI activity when tested as a heterodimer with the wild-type cleavage domain but exhibited reduced activity (42% of parental FokI) as a homodimer.

In the second round of development, we designed five constructs intended to interact favorably with E490K or E490R by hydrogen bonding with K490 or R490. All possible substitutions of positions 486 and 490 with negatively charged residues were considered as candidates for the desired interaction and were constructed individually or in combination. In initial qualitative studies, Q486D showed a dramatic loss in activity when paired with either E490K or E49OR and was not measured further. Of the remaining constructs (E490D, Q486E:E490D, Q486D:E490D, Q486E), Q486E showed the most desirable properties when paired to E490K in terms of both the highest heterodimer activity with a significant (>50%) reduction in homodimer-mediated cleavage (Table 1, "in vitro cleavage" entries).

For subsequent experiments we switched to the cellular GFP gene correction assay. Use of this system provides a means for not only gauging catalytic efficiency of the nuclease variants under consideration but also for assessing compatibility with function in a eukaryotic nucleus. For our initial studies in this system, all additional Q486X variants were generated and qualitatively screened for retention of activity when paired with E490K. Constructs passing this screen (Q486K, -M, -W, and -L, along with Q486E) were then quantitatively characterized. All five constructs exhibited high levels of gene correction activity as heterodimers with the E490K variant (Table 1, "GFP gene correction" entries), however only Q486E showed a significant reduction in homodimer activity and so this variant was chosen as the constant partner in the third round of development. In particular, as shown in FIG. 5D, the Q486E variant yielded 65% of parental FokI activity when tested as a heterodimer with the E490K domain but exhibited reduced activity (19% of parental FokI) as a homodimer.

In the third round of development, additional substitutions were made in the context of E490K with the goal of reducing homodimer function while preserving or improving activity as a heterodimer with the Q486E variant. Mutations were introduced at two positions: 486 and 538. At the 486 position, all possible amino acid substitutions were generated and qualitatively screened for activity in the GFP reporter system when paired with Q486E. Those exhibiting significant activity (generally >25% of the wt:wt pairing) were further tested quantitatively for both homodimer and heterodimer function. Two of these double mutants (E490K:Q4861 and E490K:Q486L) exhibited improvements in discrimination against homodimer function while preserving good heterodimer activity, while a third (E490K:Q486E) showed high activity and a reduction in apparent heterodimer preference (Table 1).

At the 538 position, modeling studies suggested that substitution with a basic residue might enable hydrogen bond formation with E490 on the opposite subunit. Additionally, I538 forms part of the hydrophobic pocket that interacts with I499 on the other monomer so mutations to I538 should preferentially destabilize the homodimer by disrupting both copies of the I538-I499 interaction while only disrupting one copy of this interaction as a heterodimer. In preliminary studies, both I538K and I538R were made and tested for activity when paired with the wild-type domain, and we observed that I538K retained more activity than I538R (0.87 and 0.43 of the wt:wt control respectively).

Based on this result, I538K was introduced into the E490K, E490K:Q486I and E490K:Q486E variants, and the resultant double and triple mutants were tested for gene correction activity when paired with Q486E or paired as homodimers. These studies revealed the E490K:I538K double mutant as having the best combination of high heterodimer activity and low homodimer activity (Table 1, FIG. 5D) and so this variant was chosen as the constant partner for the fourth round of development.

The fourth round of development looked for constructs that could function well when paired with E490K:I538K, but did not function well as homodimers. Various combinations of amino acid side chains were tried at positions 486, 490, and 538 but all of these lowered activity significantly when paired with E490K:I538K. A subtle change of Q486E to Q486E:I499L was also tried in the hopes that the change from Ile to Leu would disrupt the hydrophobic packing with both copies of I538 when paired as a homodimer, but not affect the packing with K538 when paired with E490K:I538K. This Q486E:I499L double mutant had the best properties in this final screen and was used in conjunction with E490K:I538K and these two variants were named the + and − variants and were extensively characterized. See, FIGS. 2, 3 and 5D. For the sake of clarity, these mutant domains will be referred to as "+" and "−" respectively, with the notation reflecting the charges of the new residues. A model of how these variants may interact at the FokI dimer interface is shown in FIG. 5E.

Example 3

Reporter Gene Correction in HEK293 Cell Line

To test the functionality of ZFNs with modified cleavage half domains, the ZFNs were evaluated in the GFP reporter assay described in U.S. Patent Publication No. 20050064474 and International Patent Publication WO2005/014791.

Briefly, a defective eGFP reporter gene containing a frameshift mutation and a fragment of the ZFN-targeted stretch of the IL2Rγ gene was generated as described in Porteus et al. supra, cloned into the pcDNA4/TO vector (Invitrogen), and stably introduced into HEK293 T-Rex cells (Invitrogen). A clonal line bearing a single integrated copy of this gene was identified and used for all experiments. The donor plasmid for correcting the defective eGFP gene was generated by cloning the functional eGFP gene (BD BioSciences) into pcDNA4/TO. To prevent GFP expression from the donor construct the first 12 bp and start codon were removed. A 1.5-kb fragment was then generated by PCR using the following primers: GGCGAGGAGCTGTTCAC (SEQ ID NO:4), TGCATACT-TCTGCCTGC (SEQ ID NO:5) (the reverse primer anneals to the pcDNA4/TO vector backbone) and cloned into pCR4Topo (Invitrogen).

HEK293 T-Rex cells (Invitrogen) were grown according to the manufacturer's instructions and transfected with the two ZFN plasmids and donor construct using LipofectAMINE™ 2000 (Invitrogen). Gene correction frequency was measured 4 days post-transfection with a Guava Easycyte™ single cell analysis system. Fluorescence at both 525 nm and 583 nm was independently measured to separate the GFP signal from autofluorescence (the GFP signal was stronger in the 525 nm channel while autofluorescence was similar in both channels). As with other similar reporter lines, the absolute gene modification frequency observed in this experiment is lower than that seen at endogenous loci due to the sequence divergence between the donor and target caused by the inserted exogenous DNA stretch.

As shown in FIG. 5F, the E490K/I538K and Q486E/I499L exhibited a strong preference for heterodimerization in the GFP gene correction reporter system. When tested for potentiation of gene correction, fusion of the "+" cleavage variant to the "L" ZFP and of the "−" variant to the "R" ZFP yielded a complex that stimulated gene correction efficiencies of 1.98% (FIG. 5F). Moreover, reversal of the ZFP-cleavage domain pairings (i.e., construction of an $L^-/R^+$ heterodimer) yielded a similarly high correction rate (1.71%). In contrast, when forced to homodimerize, both cleavage domain variants were strongly impaired, yielding correction rates of just 0.02% and 0.12% for the $L^+/R^+$ and $L^-/R^-$ homodimers respectively. By comparison, the wild-type FokI cleavage domain yielded a gene correction rate of 1.27% (FIG. 5F). Thus, the "+" and "−" variants are a potent, obligate heterodimer pair.

Example 4

Endogenous Gene Modification in K562 Cells

The function of the dimerization mutants was also confirmed at the endogenous IL2Rγ locus (exon 5) recognized by the "L" and "R" ZFPs of the fusion proteins. In particular, dimerization mutant containing ZFNs were assessed for the ability to induce a gene correction event that introduces a novel BsrBI restriction site. See, Urnov et al. (2005), supra; FIG. 6A.

Briefly, the donor plasmid used to introduce a BsrBI restriction site into exon 5 of the IL2Rγ gene has been previously described in Urnov et al. (2005), supra. For gene correction, K562 cells (ATCC) were grown to confluence in RPMI media (Gibco) supplemented with 10% FBS and split 1:4 one day before transfection. $2 \times 10^6$ cells were nucleofected with 5 µg of each ZFP plasmid and 25 µg of donor plasmid using Cell Line Nucleofector™ Kit V and Program T16 (Amaxa Biosystems) according to the manufacturer's protocol. Cells were collected 48 hours post-transfection. DNA extraction was performed with the DNeasyTm Tissue Kit (Qiagen) according to the supplier's protocol. The percentage of gene correction was determined using a PCR-based assay as essentially previously described in Urnov et al. (2005), supra, except that the PCR step used a reduced amount of genomic DNA (8 ng), was run for 24-cycles, and included 16 µCi each of $\alpha$-$^{32}$P-dCTP and $\alpha$-$^{32}$P-dATP.

The efficiency of gene correction was then quantified via PCR-amplification followed by BsrBI digestion and gel electrophoresis. Results are shown in FIG. 6B. Both the $L^+/R^-$ and $L^-/R^+$ ZFN combinations induced gene correction at levels that were both highly efficient (>10%) and indistinguishable from those induced by the $L^{wt}/R^{wt}$ ZFN combination. Importantly, forced homodimerization ($L^-/R^-$ and $L^+/R^+$) yielded no detectable gene correction in this assay (FIG. 6B, two right most lanes). Thus, the "+" and "−" variants behave as obligate heterodimers at an endogenous target.

Example 5

In vitro DNA Cleavage Assay

To further confirm the endogenous gene correction studies and GFP reporter studies evidencing that the "+" and "−" variants significantly suppress ZFN homodimer function, the following in vitro cleavage assays were performed.

Two complementary synthetic 69-mer oligonucleotides were annealed and cloned into the topo-blunt™ vector (Invitrogen) to generate each of the three sequences indicated in FIG. 7A. The ZFN target sites in each construct were verified by DNA sequencing. The verified templates were then amplified with the M13 forward and M13 reverse primers included with the topo blunt™ kit and using the recommended PCR protocol, except that the reaction was spiked with 5 µCi each of $\alpha$-$^{32}$P-dCTP and $\alpha$-$^{32}$P-dATP.

The unincorporated nucleotides were removed with a G50 spin column (GE healthcare) and the resulting mixture was diluted 100-fold in FokI buffer consisting of 20 mM Tris-HCl pH 8.5, 150 mM NaCl, 2 mM MgCl$_2$, 5% (v/v) glycerol, 10 µM ZnCl$_2$, 0.5 mg/ml BSA and 1 mM DTT. The ZFNs were expressed using the TnT-Quick™ coupled transcription/translation system (Promega) according to the manufacturer's recommendations, except that the incubation time was increased to 2 hours. The appropriate ZFNs were mixed and diluted with 1 volume of FokI buffer. A mock reaction without any starting template and diluted with 1 volume of FokI-buffer was used to make a six-fold dilution of the $L^{wt}/R^{wt}$ mixture in order to approximately normalize the activity of all three ZFN mixtures on the LR binding site. Equal volumes of diluted target site and diluted protein mixture were mixed and incubated at 37° C. for two hours. The radiolabeled DNA was then extracted with a phenol/chloroform mixture and analyzed by PAGE followed by quantification with a phosphorimager system (Molecular Dynamics).

Three radiolabeled duplexes were generated containing target sequences for either the L/R heterodimer or corresponding L/L and R/R homodimers. See, FIG. 7A. Each target was then digested by the L and R ZFNs bearing either the wild-type FokI cleavage domain ($L^{wt}/R^{wt}$) or the "+" and "−" variants in both possible configurations ($L^-/R^+$ and $L^+/R^-$).

As shown in FIG. 7B (middle and right panels), ZFNs with modified heterodimerizing cleavage domains efficiently cleaved the heterodimer target (~50% cutting) with significantly less activity against the homodimer targets. In contrast, a concentration of the $L^{wt}/R^{wt}$ unmodified dimer yielding similar levels of activity against the heterodimer target (61% cutting) also efficiently cleaved both the LL and RR targets due to homodimer formation (FIG. 7B, left panel).

Homodimer DNA cleavage activity was also tested using the heterodimer site and the same cleavage domain variant on both the L and R nucleases. FIG. 7C and Table 2 show cleavage with ZFNs comprising various pairs of wild-type and/or mutant cleavage half domains. In Table 2, numbers show the cleavage activity relative to the wild-type/wild-type pair (which was 100% cleavage under these conditions). The a and b columns indicate the identity of the cleavage domain variant in each pair. The number in the a/b column is the average of the normalized activity of L-a+R-b and of L-b+R-a; the number in the a/a column in the value of L-a+R-a; the number in the b/b column in the value of L-b+R-b.

TABLE 2

| a | b | a/b | a/a | b/b |
| --- | --- | --- | --- | --- |
| E490K | wt | 1.00 | 0.96 | 1.00 |
| Q486E | wt | 0.68 | 0.19 | 1.00 |
| E490K:I538K | wt | 0.74 | 0.00 | 1.00 |
| Q486E:I449L | wt | 0.48 | 0.00 | 1.00 |
| E490K | Q486E | 0.96 | 0.96 | 0.19 |
| E490K:I538K | Q486E | 0.32 | 0.00 | 0.19 |
| E490K | Q486E:I499L | 0.97 | 0.96 | 0.00 |
| E490K:I538K | Q486E:I449L | 0.48 | 0.00 | 0.00 |

While the E490K:I538K+Q486E:I499L pair has the lowest activity for each corresponding homodimer, this pair does have a lower activity than the wild-type nucleases. In systems with low protein expression or that utilize low affinity nucleases, other pairings such as E490K+wt or E490K+Q486E:I499L may be preferred.

These results confirmed the ability of the new variants to suppress ZFN homodimer function and increase target site specific cleavage.

Example 6

Measurement of Double-Strand Breaks in vivo

To further test the specificity of the heterodimerizing cleavage domains in the context of gene modification procedures by measuring off-target effects, the levels of genome-wide DNA cleavage were tested in mammalian cells expressing ZFNs comprising these heterodimers.

In particular, two well-validated assays for visualizing DNA double strand breaks that involve antibody-mediated detection of proteins associated with sites of DNA damage were conducted. In these studies, target cells were transfected with ZFN expression constructs alone (i.e. no donor DNA). Double-strand breaks induce phosphorylation of histone H2AX and recruitment of DNA damage response proteins such as 53BP1. Therefore, cellular straining (e.g., with antibodies to 53BP1) reveals foci around each break. See, e.g., Gorgoulis et al. (2005) *Nature* 434: 907-913. Thus, immunofluorescence assays for detecting the presence of the 53BP1 protein, which localizes to sites of DNA damage and forms foci, were conducted, essentially as described in Schultz et al. (2000) *J Cell Biol* 151:1381-1390; Anderson et al. (2001) *Mol Cell Biol* 21:1719-1729 (2001); and Rappold et al. (2001) *J Cell Biol* 153:613-620.

K562 (ATCC) cells were grown as specified above and transfected by Nucleofection™ (Amaxa Biosystems) according to the manufacturer's protocol (Solution V, Program T16). The ZFNs were co-delivered on separate plasmids except for the experiment shown in FIG. 8, in which both ZFNs were expressed from a single transcript separated by the coding region of the 2A peptide which yields each ZFN as a separate protein product also containing a portion of the 2A peptide (Szymczak et al. (2004) *Nat Biotechnol* 22: 589-594). This results in the fusion of an extra 20-residue C-terminal tag to the L ZFN, which yields migration of the L/R ZFN dimers as doublets in the Western blot in FIG. 8.

For 53BP1 immunocytochemistry,. cells were collected 1-3 days post-nucleofection and used to prepare slides by cytospin (Thermo Scientific). Cells were fixed with cold methanol and treated with 0.5% Triton X-100 buffer (0.5% Triton X-100, 1% BSA, 0.02% NaN3, PBS) at room temperature for 5 min. Cells were incubated with 5% goat serum to block non-specific staining. Cells were then incubated with anti-53BP1 rabbit polyclonal antibodies (Bethyl Laboratories, Montgomery, Tex.) followed by incubation with Alexa Fluor 594-conjugated secondary antibodies (Invitrogen-Molecular Probes) in the presence of 2.5 µg/ml of DAPI (Sigma) to counterstain cell nuclei. Slides were mounted and examined under an immunofluorescence microscope and images were acquired with a digital camera connected to the microscope.

Figure 8:
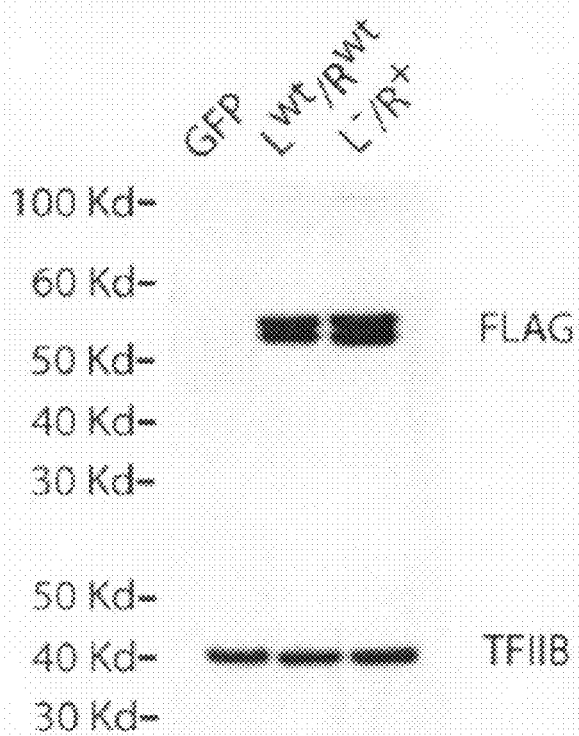
FIG. 8 depicts ZFN expression as monitored by anti-FLAG western blot. The ZFNs migrate as a doublet ("FLAG" labeled bands) due to the presence of a 20 residue C-terminal tag on the Lwt and L-ZFNs. The migration of size standards is indicated at left. TFIIB was monitored as a loading control.

Antibody-based detection of 53BP1 revealed that substitution of the heterodimer variants for the wild-type FokI cleavage domain yielded a visually dramatic reduction in the number of 53BP1 stained foci in K562 cells to levels similar to background. This observation was confirmed by quantifying the fraction of cells containing multiple foci (>3). While the fraction of such cells induced by the $L^{wt}/R^{wt}$ dimer was approximately 2.69 fold above background (43.5% vs. 16.2%), treatment with the $L^-/R^+$ dimer yielded a more modest increase (21.7% vs. 16.2%, or ~1.34 fold). This result was not due to poor expression by the $L^-/R^+$ dimer, as western blot analysis confirmed comparable levels of nuclease expression for both the $L^{wt}/R^{wt}$ and $L^-/R^+$ combinations (FIG. 8).

To confirm the 53BP1 results, we repeated these experiments using antibodies for an alternative damage marker, phosphorylated histone H2AX (γH2AX), which is generated in response to DNA damage and forms, foci at double strand breaks (see, Rogakou et al. (1998) *J Biol Chem* 273:5858-5868; Rogakou et al. (1999) *J Cell Biol* 146:905-916; and Stiff et al. (2004) *Cancer Res* 64:2390-2396 (2004).

For γH2AX flow cytometric analysis, cells were collected 1-3 days post-nucleofection, fixed with 2% paraformnaldehyde-PBS and permeabilized with penn/wash buffer (0.05% Saponin, 2.5% FBS, 0.02% NaN3, PBS). Cells were then incubated with freshly labeled anti-γH2AX monoclonal antibody (Upstate, Lake Placid, N.Y.) or freshly labeled control mouse IgG1 (Invitrogen) as a negative control; both antibodies were labeled with a Zenon R-phycoerythrin (PE) rabbit IgG labeling kit (Invitrogen-Molecular Probes, Eugene, Oreg.) according to the manufacturer's instructions. Stained cells were analyzed using a Guava Easycyte™ single cell analysis system. Fluorescence at both 525 nm and 583 nm was independently measured to separate the phycoerythrin signal from autofluorescence (compensation was used isolate the phycoerythrin signal in the 583 nm channel).

Figure 9:
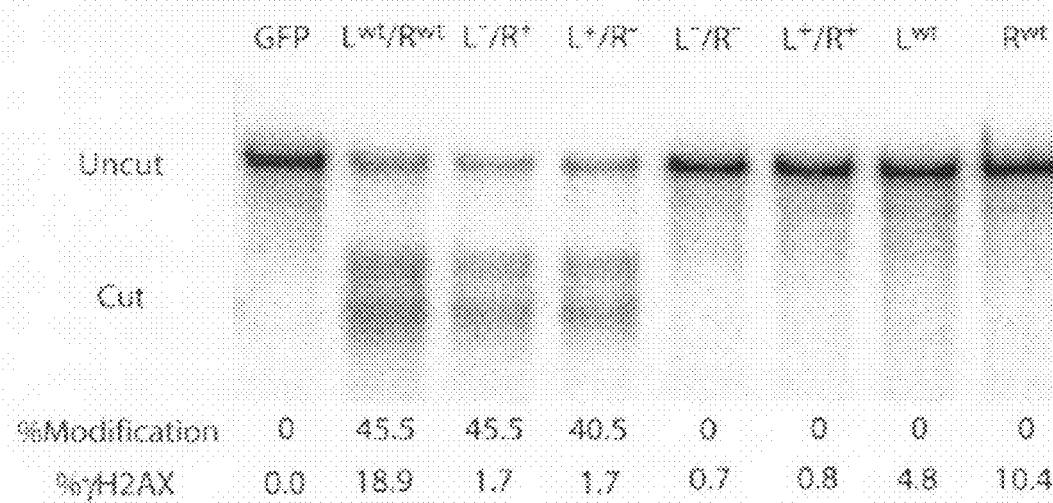
FIG. 9 depicts DNA damage and gene modification rates in K562 cells transfected with the indicated constructs. Three days after transfection, each sample was monitored for DNA damage as described in Example 6. The observed percentage of γH2AX positive cells is indicated at bottom. At the same time, gene modification rates at the IL2Rγ locus were also monitored via isolation of genomic DNA, PCR amplification of IL2Rγ exon 5 using 32P-dNTPs, reannealing of PCR products, digestion with the Surveyor™ nuclease, and analysis of digested products via polyacrylamide gel electrophoresis. An exposure of the resultant gel is shown along with deduced rates of gene modification. The % of gene modification was derived from the fraction cleaved via the formula: modification %=(1-(1-(fraction cleaved))½)×100.

Quantification relied on counting the fraction of antibody-stained cells via flow cytometry, with gates adjusted empirically to isolate the γH2AX signal from autofluorescence. Substitution of the +/− heterodimers for the wild-type FokI cleavage domain reduced the fraction of γH2AX positive cells from 18.9% to 1.7%, indicating a significant reduction in the number of off-target cleavage events induced by the variant domains. Moreover, when delivered individually both $L^{wt}$ and $R^{wt}$ yielded significant numbers of γH2AX positive cells (4.8% and 10.4% respectively) indicating that off-target cleavage via homodimerization occurs with both ZFNs in this system (FIG. 9).

Finally, to ensure that the improved genome-wide specificity was not achieved at the cost of efficacy at the intended target, we also monitored the IL2Rγ locus for ZFN-induced modification. In. the absence of donor, gene repair via non homologous end joining yields minor insertions and deletions at the site of a DSB (see, Jeggo (1998) *Adv Genet* 38:185-218), and measuring the frequency of these events provides a convenient means for gauging ZFN activity in vivo. This was accomplished via PCR-amplification of the region of interest, followed by reannealing, which converts sequence variations into mismatches and bulges. The reannealed PCR products were then digested with the Surveyor™ nuclease (Transgenomic), which preferentially cuts DNA at sites of duplex distortions (Qiu et al. (2004) *Biotechniques* 36:702-707). As shown in FIG. 9, comparable levels of amplicon were cleaved in cells treated with $L^{wt}/R^{wt}$, $L^+/R^-$ and $L^-/R^+$, indicating similar cellular activities of these ZFNs at the IL2Rγ target locus.

These studies are the first time that designed ZFNs have been directly tested in vivo for off-target cleavage and demonstrate that the heterodimer variants retained full activity for in vivo modification of their target locus while exhibiting considerably reduced levels of off-target cleavage.

In sum, these results demonstrate that Fok I mutants E490K:I538K and Q486E:I499L form obligate heterodimers. In addition, fusion polypeptides comprising these engineered cleavage half-domains stimulate gene correction at levels similar to parental Fok (as ZFP fusions) but yield fewer total cleavage events, as measured by cellular assays.

What is claimed is:

1. An in vitro method for cleaving DNA in a cell, the method comprising:
   expressing first, second, third and fourth fusion proteins in the cell, each of the fusion proteins comprising:
   (i) a zinc finger DNA-binding domain that binds to a target site in the DNA, and
   (ii) an engineered FokI cleavage half-domain;
   further wherein:
   (a) in the engineered FokI cleavage half-domain of the first fusion protein the glutamine (Q) residue at position 486 of a wild-type FokI cleavage half-domain is replaced with a glutamic acid (E) residue Q486E) or;
   (b) in the engineered FokI cleavage half-domain of the second fusion protein the glutamic acid (E) residue at position 490 of the wild-type FokI cleavage half-domain is replaced with a lysine (K) residue and the isoleucine (I) residue at position 538 of the wild-type FokI cleavage half-domain is replaced with a lysine (K) residue (E490K:I538K);
   (c) in the engineered FokI cleavage half-domain of the third fusion protein the arginine (R) residue at position 487 of the wild-type FokI cleavage half-domain is replaced with an aspartic acid (D) residue (R487D);
   (c) in the engineered FokI cleavage half-domain of the fourth fusion protein the aspartic acid (D) residue at position 483 of the wild-type FokI cleavage half-domain is replaced with an arginine (R) residue (D483R);
   (d) the first and second fusion proteins bind to first and second target sites respectively, wherein a first cleavage site lies between the first and second target sites, and
   (c) the third and fourth fusion proteins bind to third and fourth target sites respectively, wherein a second cleavage site lies between the third and fourth target sites;
   such that the first and second fusion proteins cleave the DNA at the first cleavage site, the third and fourth fusion proteins cleave the DNA at the second cleavage site.

2. The method of claim 1, wherein the DNA is in cellular chromatin.

3. The method of deleting sequences in cellular DNA, the method comprising, cleaving cellular DNA according to the method of claim 1, the DNA ends are rejoined such that sequences between the first and second cleavage sites are deleted.

4. The method of claim 3, wherein the first and second cleavage sites are on the same chromosome.

5. The method of claim 1, wherein the cell is a eukaryotic cell.

6. The method of claim 5, wherein the cell is a mammalian cell.

7. The method of claim 6, wherein the cell is a human cell.

8. The method of claim 5, wherein the cell is a plant cell.

9. A method for targeted replacement of a genomic sequence, the method comprising:
(a) cleaving a genomic DNA sequence in an isolated cell according to the method of claim 1; and
(b) contacting the cell with a donor polynucleotide, wherein the donor polynucleotide comprises:
  (i) sequences homologous to genomic sequences flanking the first and second cleavage sites; and
  (ii) an exogenous polynucleotide;
whereby genomic sequences between the first and second cleavage sites are replaced by the exogenous polynucleotide.

10. The method of claim 9, wherein the exogenous polynucleotide comprises a sequence that is homologous but non-identical sequence to the genomic sequence between the first and second cleavage sites.

11. The method of claim 10, wherein the homologous but non-identical sequence comprises a deletion with respect to the genomic sequences.

12. The method of claim 10, wherein the homologous but non-identical sequence comprises an insertion with respect to the genomic sequences.

13. The method of claim 9, wherein the exogenous polynucleotide comprises a sequence that is non-homologous to genomic sequences between the first and second cleavage sites.

14. The method of claim 9, wherein the cell is arrested in the G2 phase of the cell cycle.

15. The method of claim 9, wherein the cell is a eukaryotic cell.

16. The method of claim 15, wherein the cell is a mammalian cell.

17. The method of claim 16, wherein the cell is a human cell.

18. The method of claim 15, wherein the cell is a plant cell.

19. The method of claim 1, wherein the isoleucine residue (I) of position 499 of the engineered FokI cleavage half-domain of the first fusion protein is replaced with a leucine (L) residue (Q486E:I499L).

* * * * *